(12) United States Patent
Hasezawa et al.

(10) Patent No.: US 8,260,063 B2
(45) Date of Patent: Sep. 4, 2012

(54) FEATURE QUANTITY SELECTION METHOD, FEATURE QUANTITY SELECTION APPARATUS, IMAGE CLASSIFICATION METHOD, IMAGE CLASSIFICATION APPARATUS, COMPUTER PROGRAM, AND RECORDING MEDIUM

(75) Inventors: Seiichiro Hasezawa, Tokyo (JP); Natsumaro Kutsuna, Tokyo (JP); Takumi Higaki, Tokyo (JP); Satihiro Matsunaga, Suita (JP); Susumu Uchiyama, Suita (JP); Rika Maniwa, Suita (JP); Arni eguna Gambe, Suita (JP); Kiichi Fukui, Suita (JP)

(73) Assignee: The University of Tokyo, Tokyo (JP)

( * ) Notice: Subject to any disclaimer, the term of this patent is extended or adjusted under 35 U.S.C. 154(b) by 411 days.

(21) Appl. No.: 12/596,214

(22) PCT Filed: Apr. 18, 2008

(86) PCT No.: PCT/JP2008/001028
§ 371 (c)(1),
(2), (4) Date: Mar. 18, 2010

(87) PCT Pub. No.: WO2008/129881
PCT Pub. Date: Oct. 30, 2008

(65) Prior Publication Data
US 2010/0172555 A1 Jul. 8, 2010

(30) Foreign Application Priority Data
Apr. 18, 2007 (JP) .................................. 2007-109885

(51) Int. Cl.
*G06K 9/62* (2006.01)

(52) U.S. Cl. ....................................................... 382/225
(58) Field of Classification Search .......... 382/118–121, 382/128–134, 159–161, 224–281; 351/200–207; 235/380–385; 340/5.1–5.92; 377/10–15
See application file for complete search history.

(56) References Cited

U.S. PATENT DOCUMENTS
2003/0103652 A1* 6/2003 Lee et al. ...................... 382/118

FOREIGN PATENT DOCUMENTS
| JP | 11-213127 | 8/1999 |
| JP | 2001-134599 | 5/2001 |
| JP | 2005-253708 | 9/2005 |
| JP | 2007-080263 | 3/2007 |

OTHER PUBLICATIONS
English-language abstract of JP 2007-080263, 2007.
(Continued)

*Primary Examiner* — Atiba O Fitzpatrick
(74) *Attorney, Agent, or Firm* — Dascenzo Intellectual Property Law, P.C.

(57) ABSTRACT

A control unit (41) included in an image classification apparatus of the present invention performs a step of clustering a plurality of training images for each of a plurality of combination patterns of a plurality of feature quantities that an image has, and a step of selecting, from among the plurality of combination patterns, a classification-use combination pattern to be used in image classification, based on a result of the clustering. The clustering is performed based on degrees of similarity between the training images that have been calculated with use of the feature quantities constituting the combination patterns.

11 Claims, 24 Drawing Sheets

OTHER PUBLICATIONS

English-language abstract of JP 2005-253708, 2005.
English-language abstract of JP 2001-134599, 2001.
English-language abstract of JP 11-213127, 1999.
Shibata, Masahiro, "A Description Model of Video Content and Its Application for Video Structuring," The Translations of the Institute of Electronics, Information and Communication Engineers, vol. J78-D-II, No. 5, pp. 754-764, May 25, 1995.
International Search Report, PCT/JP2008/001028, 2 pages, Japanese Patent Office, May 27, 2008.

* cited by examiner

FEATURE QUANTITY: MAXIMUM LUMINANCE

FEATURE QUANTITY: MAXIMUM LUMINANCE

FEATURE QUANTITY SELECTION METHOD, FEATURE QUANTITY SELECTION APPARATUS, IMAGE CLASSIFICATION METHOD, IMAGE CLASSIFICATION APPARATUS, COMPUTER PROGRAM, AND RECORDING MEDIUM

TECHNICAL FIELD

The present invention relates to a feature quantity selection method for selecting image feature quantities to be used in image classification, a feature quantity selection apparatus that implements such method, a computer program for causing a computer to execute such method, a recording medium on which such computer program is recorded, an image classification method, and an image classification apparatus that implements such method.

BACKGROUND ART

Monitoring the type and condition of biological samples such as cells, intracellular structures, and biological tissue (e.g., living/dead cell, cell cycle phases) with use of an optical microscope is a key technique used when screening medical agents and variants and when evaluating the effects of chemical substances and environmental variations on an organism. Particularly in recent years, by using fluorescent proteins and vital staining reagents to selectively label specific intracellular structures (various types of organelles, cytoskeletal systems, and the like) and proteins and observe them in an alive state, it has become possible to comprehend the minute morphology of intracellular structures and the locations of various types of proteins over time, thus enabling a detailed understanding of physiological responses to exposure to medical agents, variations in environmental conditions, and the like. Accordingly, the densification of screening conditions and the refinement of biological effect evaluation references has been progressing, and also there has been rapid diversification in biological samples targeted for evaluation and in the targets of labeling. In the fields of both application and basic research, among the steps in the process of evaluating the types and conditions of biological samples, there has been progress in the automation of and an increase in the throughput of the imaging step. Meanwhile, the evaluation of obtained microscope image data is currently mainly performed by labor-intensive manual screening, and there is desire for such screening to be automated and made more efficient.

The automation of evaluating the types and conditions of biological samples (hereinafter, called "biological sample evaluation") has been mainly approached as a problem with respect to recognizing patterns in microscope images, and such automation has been realized with the use of an image classifier that classifies the types and conditions of captured images of particular biological samples into several known groups. For example, there is an apparatus that calculates feature parameters from image data of imaged cells and classifies the types of the cells with use of the feature parameters (e.g., see Patent Document 1).

Patent Document 1 discloses a cell classification apparatus that includes a parameter calculation unit that calculates feature parameters regarding the color, surface area, and shape of imaged cells from the image data of such cells, and a classification unit that classifies the cells with use of such feature parameters. Patent Document 1 also discloses that the classification unit includes a first reliability calculation unit that, based on the feature parameters, calculates a first degree of reliability indicating that a cell is a first cell, and a second reliability calculation unit that calculates, based on the feature parameters, a second degree of reliability indicating that a cell is a second cell. These first reliability calculation unit and second reliability calculation unit are configured from a neural network that has been trained using the feature parameters acquired by the parameter calculation unit as input.

Patent document 1: JP 2004-340738A

DISCLOSURE OF INVENTION

Problem to be Solved by the Invention

However, in the cell classification apparatus disclosed in Patent Document 1, if all of the feature parameters acquired by the parameter calculation unit are used as input for the first reliability calculation unit and the second reliability calculation unit, the amount of calculation involved becomes enormous, and it is possible for processing to take a disadvantageously long amount of time. Although this disadvantageous situation can be addressed by using only a portion instead of all of the feature parameters as input, this case requires the user to determine which feature parameters among all of the feature parameters are to be used as input, and this task has not been easy. In other words, the user is given the complicated task of determining whether each individual feature parameter is to be employed as input, and moreover, there is the problem that the combination of feature parameters obtained as a result of this task is not necessarily suited for image classification. Furthermore, there is the problem that determining whether a feature parameter is to be employed as input requires a considerable amount of knowledge and experience.

The present invention has been achieved in light of such situation, and an object thereof is to provide a feature quantity selection method that can select a combination pattern of image feature quantities that is suited for image classification, a feature quantity selection apparatus that implements such method, a computer program for causing a computer to execute such method, a recording medium on which such computer program is recorded, an image classification method that performs image classification using the combination pattern selected by such method, and an image classification apparatus that implements the image classification method.

Means for Solving Problem

In order to address the above issues, a feature quantity selection method of the present invention has: a step (a) of clustering a plurality of training images for each of a plurality of combination patterns of a plurality of feature quantities that an image has; and a step (b) of selecting, from among the plurality of combination patterns, a classification-use combination pattern to be used in image classification, based on a result of the clustering, wherein the clustering is performed based on degrees of similarity between the training images that have been calculated with use of the feature quantities constituting the combination patterns.

Also, in the feature quantity selection method, the step (a) and the step (b) may be performed repeatedly. In this case, preferably the plurality of combination patterns in the second and onward performances of the step (a) are a classification-use combination pattern selected in the previous performance of the step (b).

Furthermore, in the feature quantity selection method, preferably the step (a) includes a step (a1) of generating a map in which the plurality of training images are arranged at separation intervals in accordance with the degrees of similarity, and in the step (b), the classification-use combination pattern is selected based on the map. In an embodiment of the method, in the step (b), an evaluation value of the map generated in the step (a1) may be calculated based on an annotation performed on the map, and the classification-use combination pattern may be selected based on the calculated evaluation value of the map. More specifically, in another embodiment of the method, in the step (b), the evaluation value of the map generated in the step (a1) may be calculated based on an annotation performed on a portion of training images among the plurality of training images included in the map, and in another embodiment of the method, in the step (b), the clustering may be performed repeatedly with use of a combinatorial optimizing algorithm, based on the feature quantities that the image has, the combination patterns of feature quantities, and the calculated evaluation values of the maps. Furthermore, in another embodiment of the method, in the step (b), the clustering may be performed repeatedly with use of a genetic algorithm, the feature quantities that the image has respectively being genetic loci, the combination patterns of feature quantities respectively being entities having genes whose elements are the genetic loci, and the calculated evaluation values of the maps respectively being fitnesses of the entities.

The feature quantity selection method can be used in, for example, the classification of a biological sample image, and in this case, preferably the image is a captured image obtained by imaging a biological sample, and among the feature quantities are a shape feature quantity derived from a shape of the biological sample, and a texture feature quantity derived from a texture of the captured image.

Also, the present invention is a computer program for causing a computer to execute the feature quantity selection method, and a recording medium on which such computer program is recorded.

Also, in order to address the above issues, an image classification method of the present invention has: a step (a) of clustering a plurality of training images for each of a plurality of combination patterns of a plurality of feature quantities that an image has; a step (b) of selecting, from among the plurality of combination patterns, a classification-use combination pattern to be used in image classification, based on a result of the clustering; and a step (c) of classifying an input image with use of the classification-use combination pattern selected in the step (b), wherein the clustering is performed based on degrees of similarity between the training images that have been calculated with use of the feature quantities constituting the combination patterns.

Also, in order to address the above issues, a feature quantity selection apparatus of the present invention includes: a feature quantity selection unit that selects, from among a plurality of combination patterns of a plurality of feature quantities that an image has, a classification-use combination pattern to be used in image classification, the feature quantity selection unit performing a step (a) of clustering a plurality of training images for each of the plurality of combination patterns, and a step (b) of selecting the classification-use combination pattern based on a result of the clustering, wherein the clustering is performed based on degrees of similarity between the training images that have been calculated with use of the feature quantities constituting the combination patterns.

Also, in order to address the above issues, an image classification apparatus of the present invention includes: a feature quantity selection unit that selects, from among a plurality of combination patterns of a plurality of feature quantities that an image has, a classification-use combination pattern to be used in image classification; and an image classification unit that classifies an input image with use of the classification-use combination pattern selected by the feature quantity selection unit, the feature quantity selection unit performing a step (a) of clustering a plurality of training images for each of the plurality of combination patterns, and a step (b) of selecting the classification-use combination pattern based on a result of the clustering, wherein the clustering is performed based on degrees of similarity between the training images that have been calculated with use of the feature quantities constituting the combination patterns.

The above object, other objects, features, and advantages of the present invention will be apparent from the following detailed description of preferred embodiments with reference to the attached drawings.

Effects of the Invention

According to the present invention, it is possible to easily acquire a combination pattern of image feature quantities that is suited for image classification.

Figure 1:
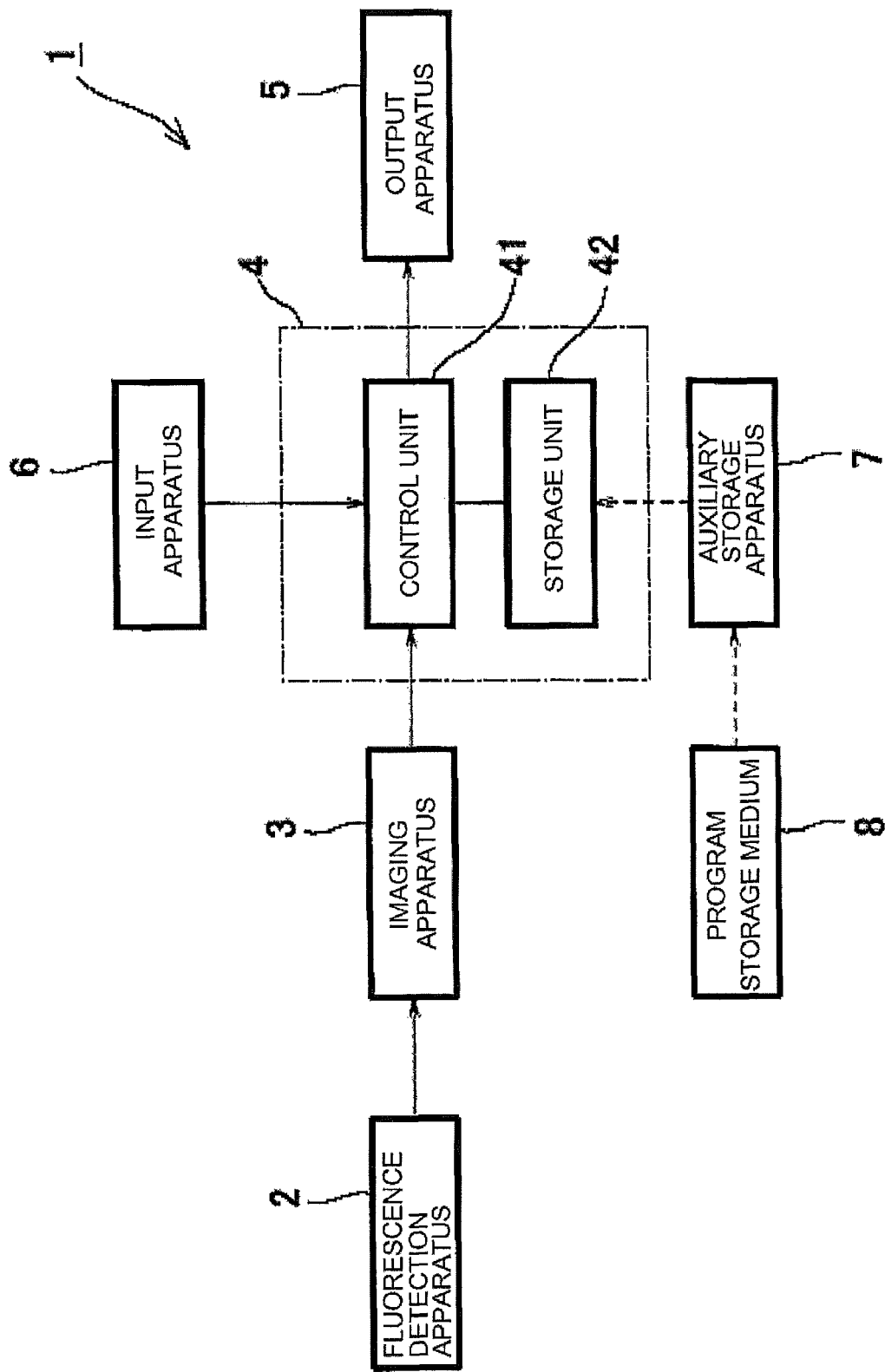
FIG. 1 is a block diagram showing a configuration of an image classification system including an image classification apparatus of the present invention.

REFERENCE SIGNS LIST 1,1a image classification system
2 fluorescence detection apparatus
2a fluorescence microscope
3 imaging apparatus
3a video camera
4 image classification apparatus
4a personal computer
5 output apparatus
5a monitor
6 input apparatus
6a keyboard
6b mouse
7 auxiliary storage apparatus
8 program storage medium
41 control unit
41a feature extractor
41b feature selector
41c feature map generator
41d feature map evaluator
41e feature selection controller
41f classifier
42 storage unit

BEST MODE FOR CARRYING OUT THE INVENTION

Below is a description of preferred embodiments of the present invention with reference to the drawings. Note that the following describes the case in which the present invention has been applied to an image classification system that classifies captured images obtained by imaging cells.

Configuration of Image Classification System

FIG. 1 is a block diagram showing a configuration of an image classification system including an image classification apparatus of the present invention. An image classification system 1 includes a fluorescence detection apparatus 2 that detects fluorescence, an imaging apparatus 3 that acquires fluorescence images derived from fluorescence detected by the fluorescence detection apparatus 2, an image classification apparatus 4 that classifies the fluorescence images acquired by the imaging apparatus 3, an output apparatus 5 that outputs a result of processing performed by the image classification apparatus 4, and an input apparatus 6 for performing various types of operations. The image classification apparatus 4 is equipped with a storage unit 42 that stores various types of data and an image classification program for executing processing that is described later, and a control unit 41 that executes the program and controls the apparatuses.

Figure 2:
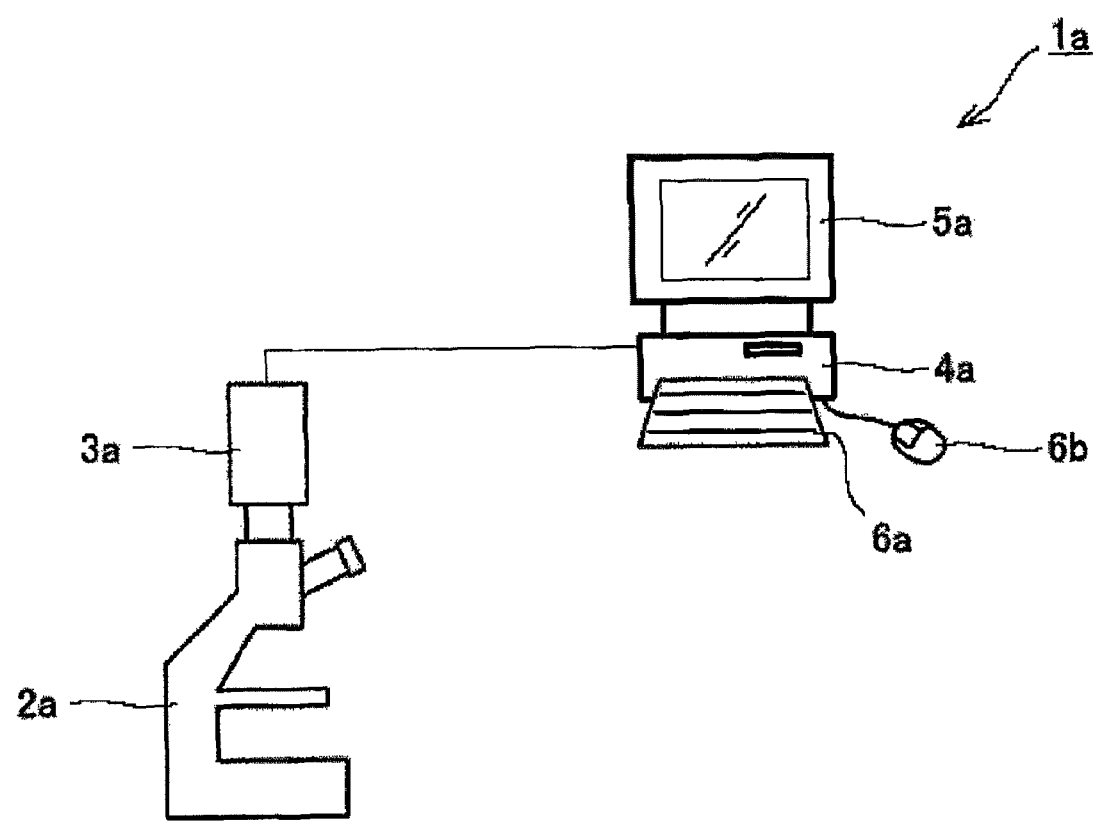
FIG. 2 is a diagram schematically showing an example of an exterior view configuration of the image classification system shown in FIG. 1.

FIG. 2 is a diagram schematically showing an example of an exterior view configuration of the image classification system shown in FIG. 1. An image classification system 1a shown in FIG. 2 includes a fluorescence microscope 2a that detects fluorescence, a video camera 3a that acquires fluorescence detected by the fluorescence microscope 2a as fluorescence images, a personal computer (hereinafter, called a PC) 4a that classifies the fluorescence images acquired by the video camera 3a, a monitor 5a that outputs a result of the classification performed by the PC 4a and the like, and a keyboard 6a and a mouse 6b that are for performing various types of operations.

It is sufficient for the fluorescence detection apparatus 2 in the image classification system 1 to be an apparatus that can detect an intensity of fluorescence emitted from a sample, and the fluorescence microscope 2a is preferably used as such apparatus, but a fluorescence scanner can also be used. The imaging apparatus 3 can be, for example, the video camera 3a that acquires image signals from the fluorescence detection apparatus 2 as two-dimensional grayscale (light/dark) images. The image classification apparatus 4 can be configured from, for example, a microcomputer including an image processing circuit that can process images captured at a constant interval in real-time, as well as a CPU, a ROM, a RAM, and an I/O port. The image classification apparatus 4 can also be configured by, for example, the PC 4a. Although the storage unit 42 of the image classification apparatus 4 is configured from a ROM and a RAM and has the image classification program stored therein, the image classification program may be recorded on a program recording medium 8 such as a flexible disk or a CD-ROM, and may be read to the storage unit 42 via an auxiliary storage apparatus 7 (a flexible disk drive, CD-ROM drive, or the like) that is an apparatus that mechanically performs reading from and writing to the program recording medium 8. The output apparatus 5 can be, for example, the monitor 5a that displays information on a CRT or liquid crystal display, or a printing apparatus that prints information onto a sheet, such as a laser printer. The input apparatus 6 can be the keyboard 6a, the mouse 6b, and the like.

Figure 3:
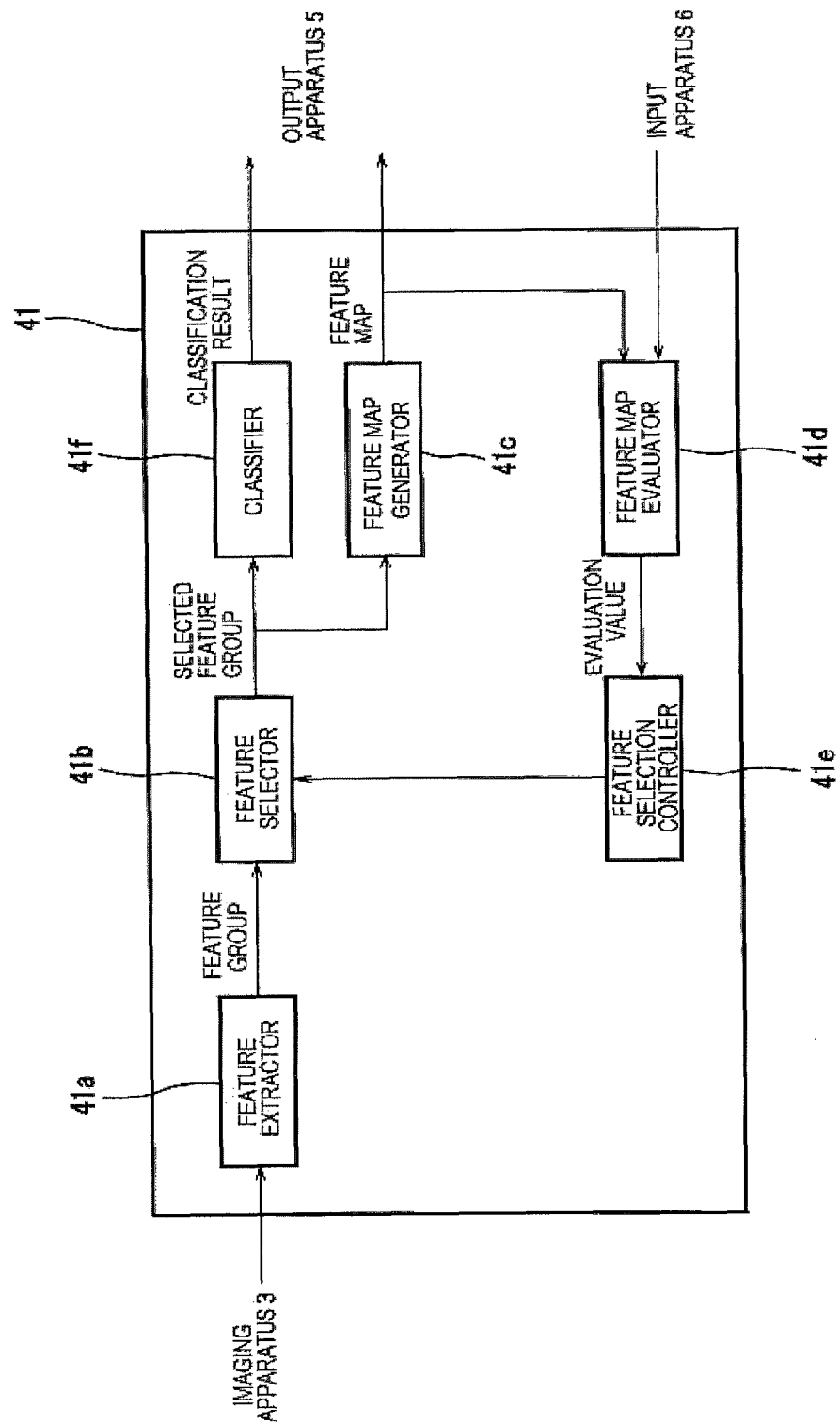
FIG. 3 is a function block diagram showing a configuration of a control unit included in the image classification apparatus.

FIG. 3 is a function block diagram showing a configuration of the control unit 41 included in the image classification apparatus 4. As shown in FIG. 3, the control unit 41 includes a feature extractor 41a that extracts image feature quantities, a feature selector 41b that selects specific feature quantities from among the feature quantities extracted by the feature extractor 41a, a feature map generator 41c that generates a later-described feature map with use of the feature quantities selected by the feature selector 41b, a feature map evaluator 41d that evaluates the feature map generated by the feature map generator 41c, a feature selection controller 41e that controls the selection of feature quantities by the feature selector 41b, and a classifier 41f that performs image classification with use of the feature quantities selected as being optimal for image classification. The feature extractor 41a, the feature selector 41b, the feature map generator 41c, the feature map evaluator 41d, the feature selection controller 41e, and the classifier 41f are realized as modules in the image classification program.

The image classification apparatus 4 of the present invention that is included in the image classification system 1 also functions as a feature quantity selection apparatus of the present invention. In the following, the operations of the image classification apparatus 4 are described separately in two modes, namely (1) a classifier generation mode and (2) a classification mode, and of these two modes, the operations in (1) the classifier generation mode correspond to operations performed as the feature quantity selection apparatus of the present invention, and such operations plus the operations in (2) the classification mode correspond to operations performed as the image classification apparatus of the present invention.

Operations of Image Classification Apparatus

As described above, the image classification apparatus 4 of the present invention has two operation modes, namely (1) the classifier generation mode and (2) the classification mode. As is described later, (1) the classifier generation mode involves the clustering of training images, and the selection of feature quantities and generation of a classifier based on the result of such clustering, and (2) the classification mode involves performing image classification with use of the selected feature quantities and generated classifier.

Here, the term clustering refers to automatically performing classification without an external reference, and is a so-called "unsupervised classification method". With clustering, a measure indicating the association between two arbitrary data pieces in a data group to be classified is assumed to have been defined, the data group is divided into several lumps (clusters), and grouping is performed so that the degree of association between data pieces is high in each cluster, and the degree of association between different groups is low. Accordingly, when classification is performed based on the result of such clustering, various image data pieces will be classified such that image data pieces with a high degree of association belong to the same cluster, without the need for, for example, preliminary processing for setting an external reference.

(1) Classifier Generation Mode

In the classifier generation mode, after the processing performed by the feature extractor 41a has ended, the feature selector 41b, feature map generator 41c, feature map evaluator 41d, and feature selection controller 41e modules repeatedly perform the processing described below until a combination pattern suited for image classification has been selected from among a plurality of image feature quantity combination patterns. The clustering of training images is performed by the repeated execution of the processing in these modules.

Figure 4:
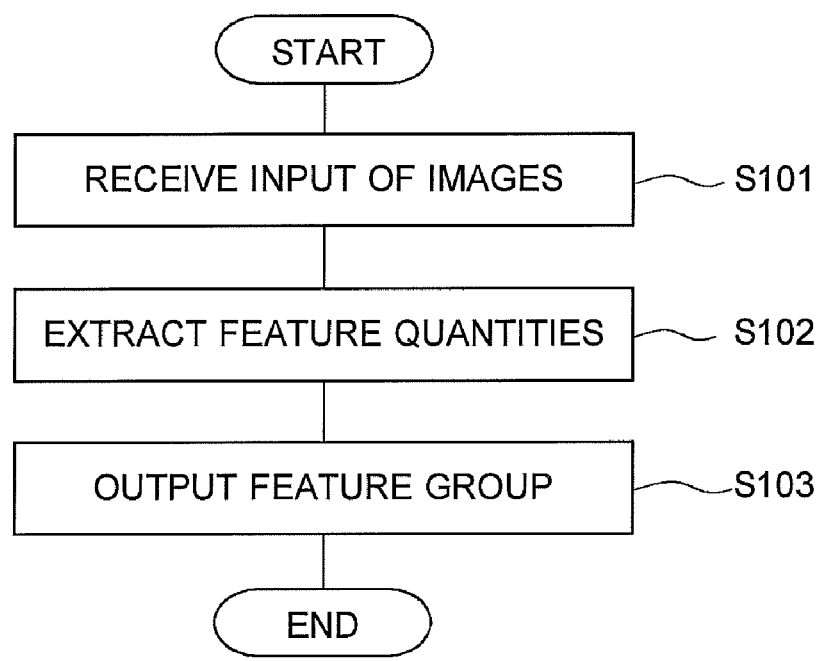
FIG. 4 is a flowchart showing a flow of operations performed by a feature extractor in a classifier generation mode.

FIG. 4 is a flowchart showing a flow of operations performed by the feature extractor 41a in the classifier generation mode. First, the feature extractor 41a receives, from the imaging apparatus 3, an input of a plurality of images that have been captured by the imaging apparatus 3 (S101). Hereinafter, these input images are called training images.

Next, the feature extractor 41a extracts a plurality of feature quantities that the input images have (S102), and outputs the extracted feature quantities to the feature selector 41b as feature groups (S103).

If the training images are time-series images, the feature extractor 41a analyzes each image at each time point, and performs steps S102 and S103 for each analyzed image, thus outputting a feature group for each time point to the feature selector 41b. In this case, the processing in each subsequent module is performed separately for each image at each time point. Note that information regarding the temporal relationship between the training images is stored in the storage unit 42 since such information is used by later-stage modules.

Also, if the training images are multiband images captured at a plurality of fluorescence wavelengths (e.g., if the nucleus and microtubule of a cell are fluorescently-labeled using red and green respectively and are both captured in an image), the feature extractor 41a generates a grayscale image group after performing analysis for each band, and extracts feature quantities for each of the grayscale images.

The number of types of feature quantities extracted by the feature extractor 41a is approximately 150 if the training images are in a simplest image format. Examples of these feature quantities include shape feature quantities derived from the shape of the imaging target, and texture feature quantities derived from the texture of the imaging target.

The shape feature quantities in the present embodiment are numerical value groups obtained by calculating, with respect to a white region extracted from a black and white image obtained from a training image by determining a threshold value by a discriminant analysis method, for example a surface area, perimeter, circularity, major axis length, minor axis length, major axis to minor axis ratio, complexity, and luminance distribution (average, median, standard deviation, skewness, kurtosis) of an area corresponding to the white region in the training image.

The texture feature quantities in the present embodiment are numerical value groups obtained by measuring form parameters such as the surface area, perimeter, number, and complexity of imaging targets by extracting white regions and black regions for each image in a black and white image group (16 types) obtained by binarizing training images according to 16 types of threshold values obtained by equally dividing the luminance range from lowest luminance to highest luminance into 18 levels, and then calculating statistical quantities (average, maximum, variance, median) of the entire group of 16 types of images for each form parameter, and these texture feature quantities include so-called multi-shape feature quantities. Note that in addition to being performed on grayscale images, the extraction of such shape feature quantities is performed on boundary images obtained by applying a Sobel filter as pre-processing.

The texture feature quantities also include values calculated based on the luminance of an image as a whole, that is to say, numerical value groups focusing on the average luminance, maximum luminance, luminance variance, luminance histogram, and degree of association between the luminance of adjacent pixels (difference and product), which are also called luminance feature quantities. Table 1 shows examples of feature quantities extracted by the feature extractor 41a.

TABLE 1

Feature quantities extracted by feature extractor

| Broad classification of feature quantities | Intermediate classification of feature quantities | Detailed classification of feature quantities | Feature quantities |
|---|---|---|---|
| Grayscale image | Shape feature | Feature of overall shape | Surface area, perimeter, circularity, major axis length, minor axis length, major axis to minor axis ratio, complexity |
| | | Feature of individual shapes | Average surface area, average perimeter, average of major axis to minor axis ratio, average circularity |
| | | Luminance distribution feature within a shape | Average, median, standard deviation, skewness, kurtosis |
| | Texture feature | Luminance distribution feature of overall image | Minimum value, maximum value, spread, average, median, difference between average and median, standard deviation, standard deviation/spread, skewness, kurtosis |
| | | Gray-level co-occurrence matrix (GLCM) | Homogeneity, contrast, standard deviation, average, entropy, skewness |
| | | Multi-shape feature | Distribution of number of individual shapes in high luminance regions: maximum value, average, luminance yielding average, median, standard deviation |
| | | | Distribution of number of individual shapes in low luminance regions: maximum value, average, luminance yielding average, median, standard deviation |
| | | | Distribution of complexity in high luminance regions: maximum value, average, luminance yielding average, median, standard deviation |
| | | | Distribution of complexity in low luminance regions: maximum value, average, luminance yielding average, median, standard deviation |
| | | | Distribution of displacement in high luminance regions: maximum value, average, luminance yielding average, median, standard deviation |
| | | | Distribution of displacement in low luminance regions: maximum value, average, luminance yielding average, median, standard deviation |
| | | | Distribution of inertia moment in high luminance regions: maximum value, average, luminance yielding average, median, standard deviation |
| | | | Distribution of inertia moment in low luminance regions: maximum value, average, luminance yielding average, median, standard deviation |
| | | | Distribution of total surface area in high luminance regions: maximum value, average, luminance yielding average, median, standard deviation |
| | | | Distribution of total surface area in low luminance regions: maximum value, average, luminance yielding average, median, standard deviation |
| | | | Distribution of average surface area in high luminance regions: maximum value, average, luminance yielding average, median, standard deviation |
| | | | Distribution of average surface area in low luminance regions: maximum value, average, luminance yielding average, median, standard deviation |
| Boundary image | Shape feature | Feature of overall shape | Surface area, perimeter, circularity, major axis length, minor axis length, major axis to minor axis ratio, complexity |
| | | Feature of individual shapes | Average surface area, average perimeter, average of major axis to minor axis ratio, average circularity |
| | | Luminance distribution feature within a shape | Average, median, standard deviation, skewness, kurtosis |
| | Texture feature | Luminance distribution feature of overall image | Minimum value, maximum value, spread, average, median, difference between average and median, standard deviation, standard deviation/spread, skewness, kurtosis |
| | | Gray-level co-occurrence matrix (GLCM) | Homogeneity, contrast, standard deviation, average, entropy, skewness |
| | | Multi-shape feature | Distribution of number of individual shapes in high luminance regions: maximum value, average, luminance yielding average, median, standard deviation |
| | | | Distribution of number of individual shapes in low luminance regions: maximum value, average, luminance yielding average, median, standard deviation |
| | | | Distribution of complexity in high luminance regions: maximum value, average, luminance yielding average, median, standard deviation |
| | | | Distribution of complexity in low luminance regions: maximum value, average, luminance yielding average, median, standard deviation |
| | | | Distribution of displacement in high luminance regions: maximum value, average, luminance yielding average, median, standard deviation |
| | | | Distribution of displacement in low luminance regions: maximum value, average, luminance yielding average, median, standard deviation |
| | | | Distribution of inertia moment in high luminance regions: maximum value, average, luminance yielding average, median, standard deviation |
| | | | Distribution of inertia moment in low luminance regions: maximum value, average, luminance yielding average, median, standard deviation |
| | | | Distribution of total surface area in high luminance regions: maximum value, average, luminance yielding average, median, standard deviation |
| | | | Distribution of total surface area in low luminance regions: maximum value, average, luminance yielding average, median, standard deviation |
| | | | Distribution of average surface area in high luminance regions: maximum value, average, luminance yielding average, median, standard deviation |
| | | | Distribution of average surface area in low luminance regions: maximum value, average, luminance yielding average, median, standard deviation |

Note that if the training images are time-series images, in the last stage of the feature quantity extraction processing, the feature extractor 41a calculates the difference between each feature quantity and the feature quantity from the previous time point, and adds the calculated differences as feature groups.

For example, if the imaging target is a chromosome of a cell, the shape feature quantities (form parameters) are those shown in Table 2, and the texture feature quantities are those shown in Table 3.

TABLE 2

| Form parameter | Abbreviation | Description |
| --- | --- | --- |
| Surface area | AREA | Surface area of chromosome |
| Major axis | MAJ | Length of long axis that traverses entire ellipse of mitotic chromosome |
| Minor axis | MIN | Length of short axis that traverses entire ellipse of mitotic chromosome |
| Feret's diameter | FERET | Longest distance between 2 points along circumference of chromosome region |
| Perimeter | PERI | Length of line enclosing the chromosome region |
| Equivalent diameter | EQD | $\left(\dfrac{4 \times \text{AREA}}{\pi}\right)^{1/2}$ |
| Area enclosed in square | EB | Product of multiplication of major axis and minor axis |
| Roundness | RND | $\dfrac{4 \times \text{AREA}}{\pi \times \text{MAJ}}$ |
| Convex face diameter | CNVXP | $\left(\dfrac{4 \times \pi \times \text{AREA}}{\text{RND}}\right)^{1/\sqrt{2}}$ |
| Ratio of EQD to FERET | EF | Ratio of equivalent diameter to Feret's diameter |
| Ratio of FERE to MIN | FMIN | Ratio of Feret's diameter to minor axis |
| Ratio of EQD to MIN | EMIN | Ratio of equivalent diameter to minor axis |
| Ratio of EQD to MAJ | EMAJ | Ratio of equivalent diameter to major axis |
| Compactness | CMPCT | $\dfrac{\left(\dfrac{4 \times \text{AREA}}{\pi}\right)^{1/2}}{\text{MAJ}}$ |
| Aspect ratio | AR | Ratio of major axis to minor axis |
| Eccentricity | ECC | Quantitative measurement of ellipse. Ellipse is more circular as this value approaches 0. |
| Center of gravity | CEN | Central point of selected region. Average of x and y coordinates of all pixels in selected region. |
| Circularity | CIRC | 4 × π × AREA/PERI. A value of 1 indicates a perfect circle. The closer this value is to 0, the more elongated the polygon is. |
| Height of boundary frame | H | Height of boundary frame that covers entire chromosome region |
| Distance between centers of gravity | DIST | Distance between centers of gravity of cell in anaphase, telophase, or cytokinesis (ATC) |
| Sum of DIST times average H plus EB | DISTH | Distance between centers of gravity of ATC mitotic chromosome is multiplied by average height of boundary frame, and the area of the surrounding square is added to the result. (DIST × average H) + EB |
| Sum of difference between EB and AREA | SEBA | Sum of absolute values of differences between surface area of mitotic chromosome and area of surrounding square |
| Sum of EB | SEB | Sum of areas of squares surrounding mitotic chromosomes |
| Sum of AREA | SAREA | Sum of surface areas of mitotic chromosomes |
| Sum of EQD | SEQD | Sum of equivalent diameters of mitotic chromosomes |
| Sum of PERI | SPERI | Sum of perimeters of mitotic chromosomes |
| Sum of CNVXP | SCNVXP | Sum of convex face diameters of mitotic chromosomes |
| Sum of ratios of EB to RND | SEBR | Sum of ratios of area of square surrounding mitotic chromosome to roundness |
| Sum of ratios of EB to CIRC | SEBC | Sum of ratios of area of square surrounding mitotic chromosome to circularity |
| Sum of FERET | SFERET | Sum of Feret's diameters of mitotic chromosomes |

TABLE 3

| Texture parameters (Abbreviation) | Description, expression, citation |
|---|---|
| Homogeneity | $\sum_{i,j} \dfrac{p(i,j)}{1+|i-j|}$ <br><br> Measure of uniformity of images obtained from the gray-level co-occurrence matrix (GLCM). See citation 1. |
| Contrast | $\sum_{i,j} |i-j|^2 p(i,j)$ <br><br> Measure of contrast obtained from the gray-level co-occurrence matrix (GLCM). See citation 1. |
| Standard Deviation ($\sigma$) | $\sigma = \sqrt{\sigma^2} = \sqrt{\mu_2(z)} = \sqrt{\sum_{i=0}^{L-1}(z_i - m)^2 h(z_i)}$ <br><br> Measure of variance in a distribution of a luminance histogram. See citation 2. |
| Mean (m) | $m = \sum_{i=0}^{L-1} z_i h(z_i)$ <br><br> Measure of average luminance. See citation 2. |
| Entropy (e) | $e = \sum_{i=0}^{L-1} h(z_i) \log_2 h(z_i)$ <br><br> Measure of disorderliness. See citation 2. |
| Moment invariant | Feature quantity used in curve recognition. See citation 2. |
| Third Moment ($\mu_3$) | $\mu_3 = \sum_{i=0}^{L-1}(z_i - m)^3 h(z_i)$ <br><br> Skewness of luminance histogram. See citation 2. |

Notes:
p(i, j) is a correction value that expresses the probability that; from the viewpoint of a pixel having a luminance i, the luminance of the pixel adjacent to the right is j (in this case, referred to as "H.O."), or the probability that the luminance of a pixel adjacent above, to the upperright, or to the right is j (in this case, referred to as "M.O.").
$h(z_i)$ is the occurrence probability of a pixel having a luminance $z_i$.
However, $1 = \sum_{i=0}^{L-1} h(z_i)$. Note that L is the number of image quantization levels, and the value of L is 4096.
Citation 1:
Mathworks. http://www.mathworks.com/access/helpdesk/help/toolbox/images/f11-29651.html
Citation 2:
Gonzalez, R.C., R. Woods, S. Eddins. (2004). Digital Image Processing Using MATLAB®. Pearson Education Institute, Pearson Prentice Hall, Pearson Education, Inc. Upper Saddle River, N.J, USA.

Figure 5:
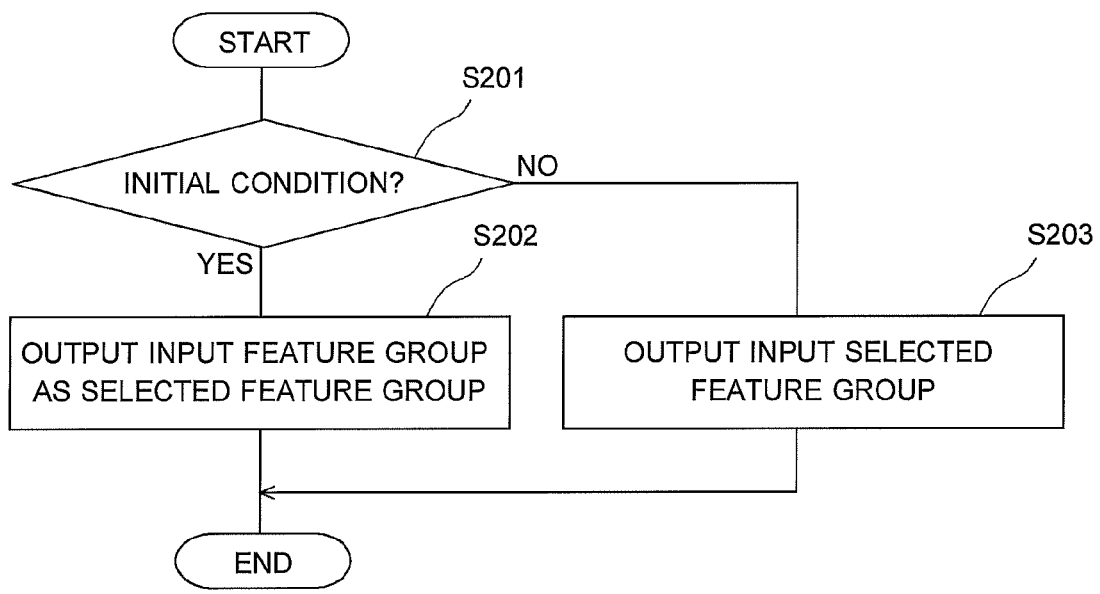
FIG. 5 is a flowchart showing a flow of operations performed by a feature selector in the classifier generation mode.

FIG. 5 is a flowchart showing a flow of operations performed by the feature selector 41b in the classifier generation mode. The feature selector 41b determines whether the state is the initial state (S201), and if the state has been determined to be the initial state (S201:YES), the feature selector 41b outputs, to the feature map generator 41c, the feature groups input from the feature extractor 41a as feature groups that have been selected (selected feature groups) (S202).

On the other hand, if the state has been determined to not be the initial state (S201:NO), the feature selector 41b outputs, to the feature map generator 41c, selected feature groups that have been input from the feature selection controller 41e as described later (S203). In this way, the feature selector 41b is controlled by the feature selection controller 41e.

Figure 6:
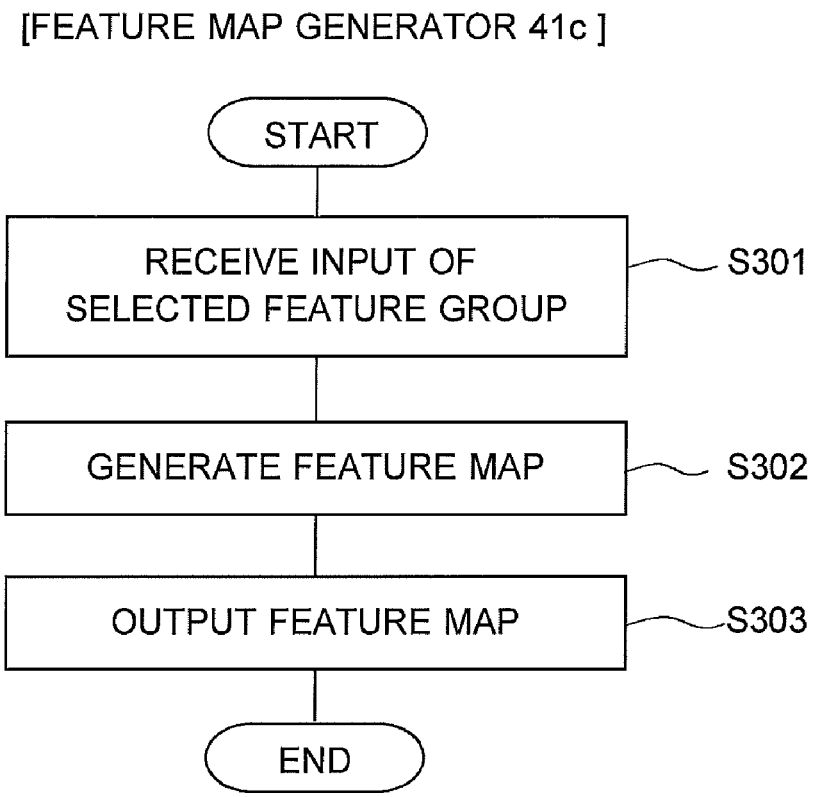
FIG. 6 is a flowchart showing a flow of operations performed by a feature map generator in the classifier generation mode.

FIG. 6 is a flowchart showing a flow of operations performed by the feature map generator 41c in the classifier generation mode. First, the feature map generator 41c receives an input of the selected feature groups from the feature selector 41b (S301). In this case, the feature map generator 41c receives an input of selected feature groups for all of the training images simultaneously. Next, the feature map generator 41c calculates degrees of similarity between the training images, generates a feature map in which the plurality of training images are arranged at intervals of separation in accordance with the degrees of similarity (S302), and outputs the generated feature map to the output apparatus 5 and the feature map evaluator 41d. Thereafter, the output apparatus 5 displays the feature map on a screen. The following is a detailed description of the feature map.

In the present embodiment, the feature map generation processing executed by the feature map generator 41c is performed with use of an SOM (Self-Organizing Map) method. Specifically, the feature map is generated by calculating degrees of similarity between the training images with use of the selected feature quantities of the training images, and mapping the training images on a two-dimensional plane such that the training images are arranged at intervals of separation in accordance with the degrees of similarity. This feature map is a graphic expressing the degree of similarity between each of the training images and the mutual degree of association within training image groups.

Figure 11:
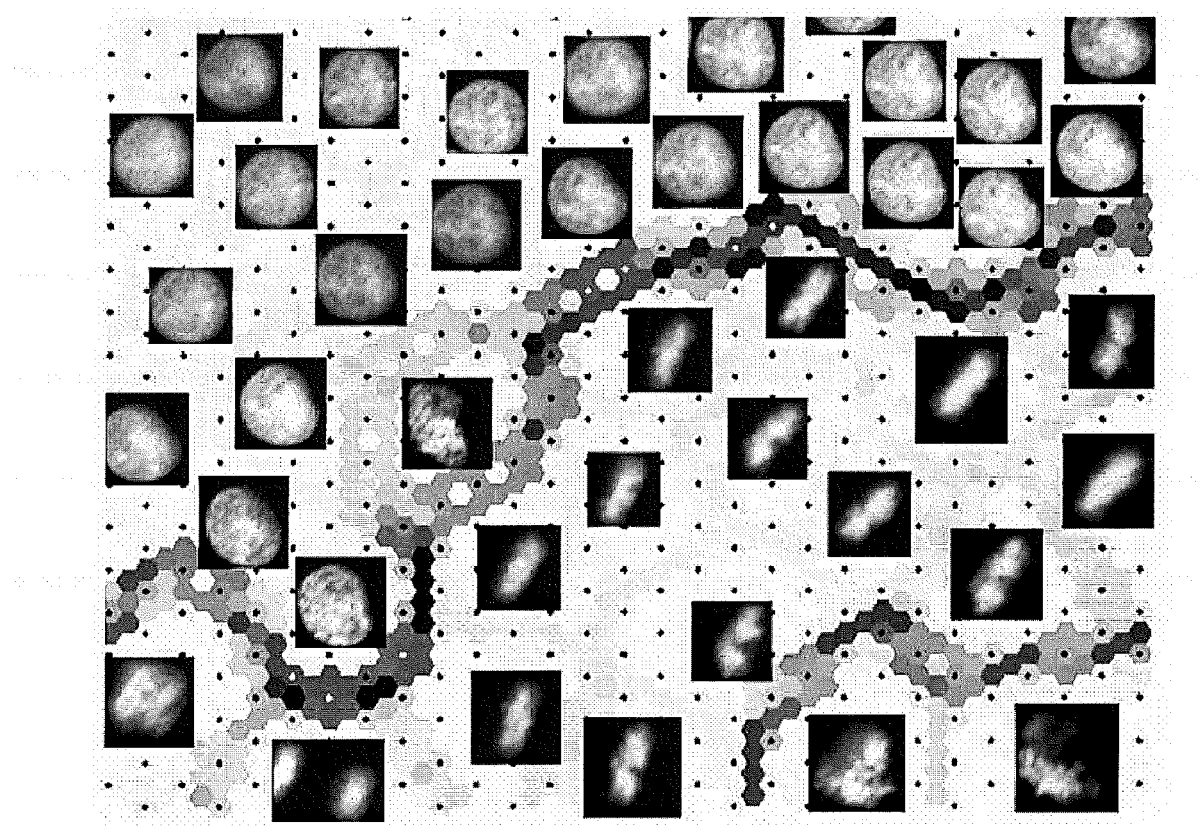
FIG. 11 is a diagram showing an example of a feature map that has been generated by the feature map generator and is to be displayed on the screen of an output apparatus.

FIG. 11 shows an example of a feature map that has been generated by the feature map generator 41c and displayed on the screen of the output apparatus 5. As shown in FIG. 11, the feature map is divided into equal regions (nodes) by a regular hexagonal grid, and each of the training images are mapped to one of the nodes. Although there are 144 nodes in the example shown in FIG. 11, the number of nodes can be adjusted appropriately in accordance with the number of training images. In the feature map, similar images are arranged on adjacent nodes or on the same node. Here, the measure of similarity is prescribed by the selected feature groups input to the feature map generator 41c. Also, a value indicating the degree of similarity between nodes (inter-node degree of similarity) has been assigned at each boundary between a pair of adjacent nodes in the feature map (in FIG. 11, expressed by lightness/darkness).

If the training images are time-series images, in addition to the images at each time point being individually arranged on the feature map, trajectories expressed by line segments connecting the images are displayed on the feature map as information indicating the temporal relationship between the time points.

Note that a degree of similarity calculated by the feature map generator 41c in the present embodiment can be defined as a Euclidean distance d (Fa,Fb) between "selected feature group (including 1 or more numerical data pieces) Fa of image a" and "selected feature group (including 1 or more numerical data pieces) Fb of image b", and if Fa and Fb are respectively expressed as Fa=(a1, a2, a3, ... an) and Fb=(b1, b2, b3, ... bn), that is to say, as a combination of n feature quantities, the degree of similarity is calculated according to Expression 1 shown below.

Expression 1

$$d(Fa, Fb) = \sqrt{\left(\sum_{i=1}^{n}(ai - bi)^2\right)}$$

Expression 1

Figure 7:
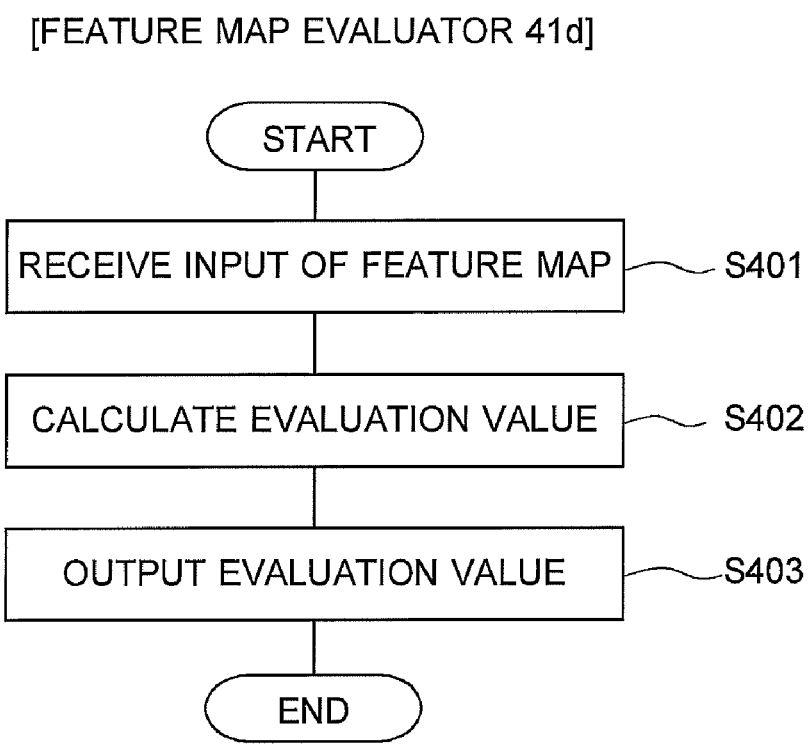
FIG. 7 is a flowchart showing a flow of operations performed by a feature map evaluator in the classifier generation mode.

FIG. 7 is a flowchart showing a flow of operations performed by the feature map evaluator 41d in the classifier generation mode. The feature map evaluator 41d receives an input of the feature map from the feature map generator 41c (S401). Next, the feature map evaluator 41d calculates, as an evaluation value, a real value from 0 to 1 inclusive that indicates the degree to which the feature map reflects the distribution of conditions of the imaging targets in the training image group (S402), and outputs the calculated evaluation value to the feature selection controller 41e (S403). The following is a detailed description of the evaluation of the feature map.

The evaluation reference in the evaluation of the feature map performed by the feature map evaluator 41d is set upon receiving an annotation that is a user instruction of a classification reference. In other words, the feature map evaluator 41d evaluates the feature map based on an annotation to the feature map.

As described above, although the feature map evaluator 41d performs operations repeatedly in the classifier generation mode, at the first instance of operation in particular, the feature map evaluator 41d waits for an instruction from the user, and an annotation step is performed. However, if the training image group is a plurality of time-series images, the annotation step can be omitted at this point in time.

Figure 12:
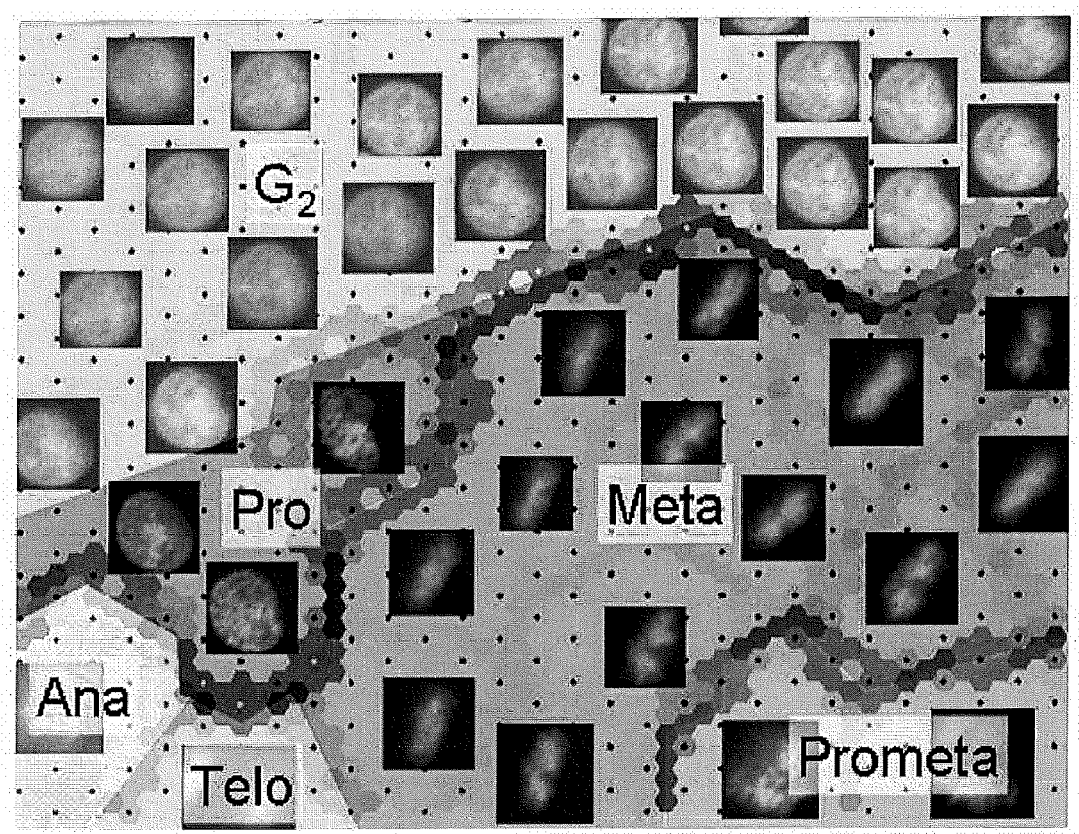
FIG. 12 is a diagram showing an example of a feature map in the case in which an annotation step has been implemented.

In the present embodiment, the annotation step is implemented by the user observing the feature map displayed on the screen of the output apparatus 5, and inputting, with use of the input apparatus 6, which regions on the feature map correspond to which conditions. FIG. 12 shows an example of a feature map in the case in which the annotation step has been implemented. In FIG. 12, Pro indicates the prophase, Prometa indicates the prometaphase, Meta indicates the metaphase, Ana indicates the anaphase, Telo indicates the telophase, and G2 indicates the G2 phase (interphase immediately before the cell division phase).

If the training image group is not a group of time-series images, the feature map evaluator 41d calculates a feature map evaluation value based on teacher data obtained from the annotation. Specifically, the evaluation value is calculated by performing normalization by, in the feature map, dividing the "sum of the inter-node degrees of similarity for all pairs of adjacent nodes corresponding to boundaries between classes" by the "sum of all of the inter-node degrees of similarity", and then subtracting the normalized value from 1.

Also, in the case in which the training images are time-series images, and the annotation step is omitted in the initial instance of operation, the evaluation value is obtained by performing normalization by dividing the "distance between trajectories indicating transitions in the condition of the imaging targets" by the "sum of all of the inter-node degrees of similarity", and then subtracting the normalized value from 1.

A higher evaluation value calculated in this way indicates that the feature groups selected by the feature selector 41b two stages ago is more suited for classifying the conditions of the imaging targets in accordance with the annotation.

Figure 8:
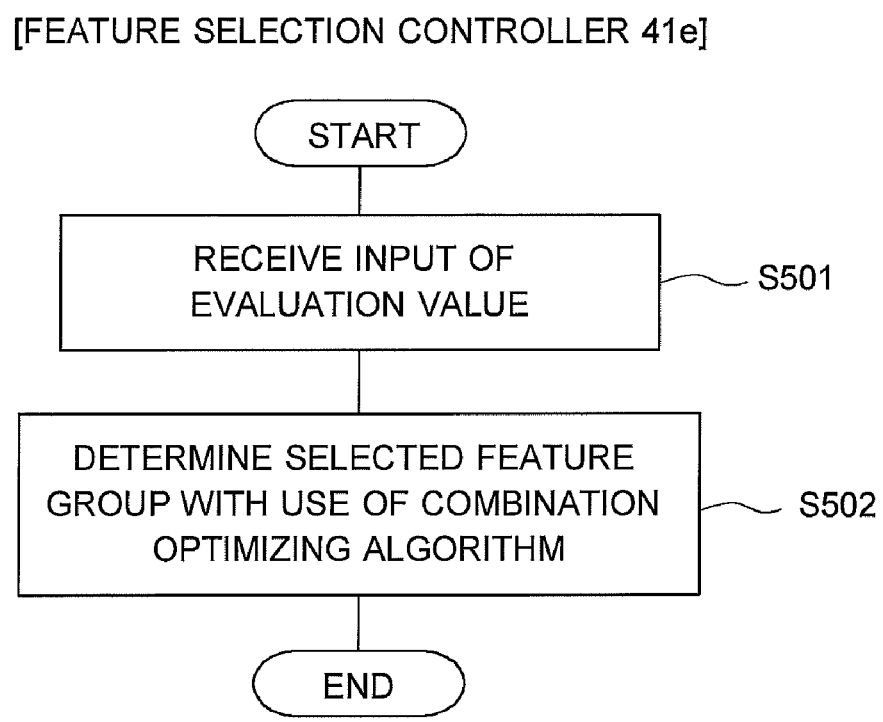
FIG. 8 is a flowchart showing a flow of operations performed by a feature selection controller in the classifier generation mode.

FIG. 8 is a flowchart showing a flow of operations performed by the feature selection controller 41e in the classifier generation mode. The feature selection controller 41e receives an input of the feature map evaluation value from the feature map evaluator 41d (S501). Then, the feature selection controller 41e determines, with use of a combinatorial optimizing algorithm, selected feature groups that are a feature quantity combination pattern that causes the evaluation value to be maximal (S502). Specifically, the selected feature groups that are superior as a reference for evaluating the conditions of the imaging targets are determined by searching the plurality of feature quantities output from the feature extractor 41a for the combination of feature quantities that causes the feature map evaluation value to be maximal (i.e., enables the conditions of the imaging targets to be appropriately evaluated). Accordingly, the feature selection controller 41e optimizes the feature selector 41b.

Note that letting M be the number of types of feature quantities output from the feature extractor 41a, the number of feature quantity combinations is 2 to the power of M. Since M is normally a value of several hundred or more, generating a feature map for each combination and evaluating each feature map is not realistic due to constraints on the computational time. For this reason, a combinatorial optimizing algorithm that quickly searches for an approximate solution is used. In the present embodiment, a genetic algorithm (GA) is employed as the combinatorial optimizing algorithm.

A GA is an optimization technique inspired by the evolution of organisms through natural selection, and an approximate solution to a given problem is obtained by setting each candidate solution as an "entity", likening the validity of each candidate solution to a "fitness", and repeatedly performing the steps of obtaining the fitness of each entity constituting an entity group, generating a next-generation entity group by selecting and crossbreeding entities with high degrees of fitness, and then obtaining the fitness of each entity in group of next-generation entities. In the present embodiment, the "given problem" is "selecting features suited for classifying the conditions of biological samples in accordance with an annotation", the "entities" correspond to "types of feature quantities selected by the feature selector 41b", and the "fitness" corresponds to the "evaluation value obtained by the feature map evaluator 41d". Specifically, each feature quantity extracted from the training images is treated as a 1-bit "genetic locus", where if the value of the genetic locus is 1, the corresponding feature quantity is selected by the feature selector 41b and used in the subsequent generation of a feature map, and if the value is 0, the corresponding feature quantity is not selected and not used in the subsequent generation of a feature map. The number of genetic loci is equal to M, which is the number of feature quantity types, and therefore an M-bit "gene" is the genetic pattern of a GA "entity".

Figure 9:
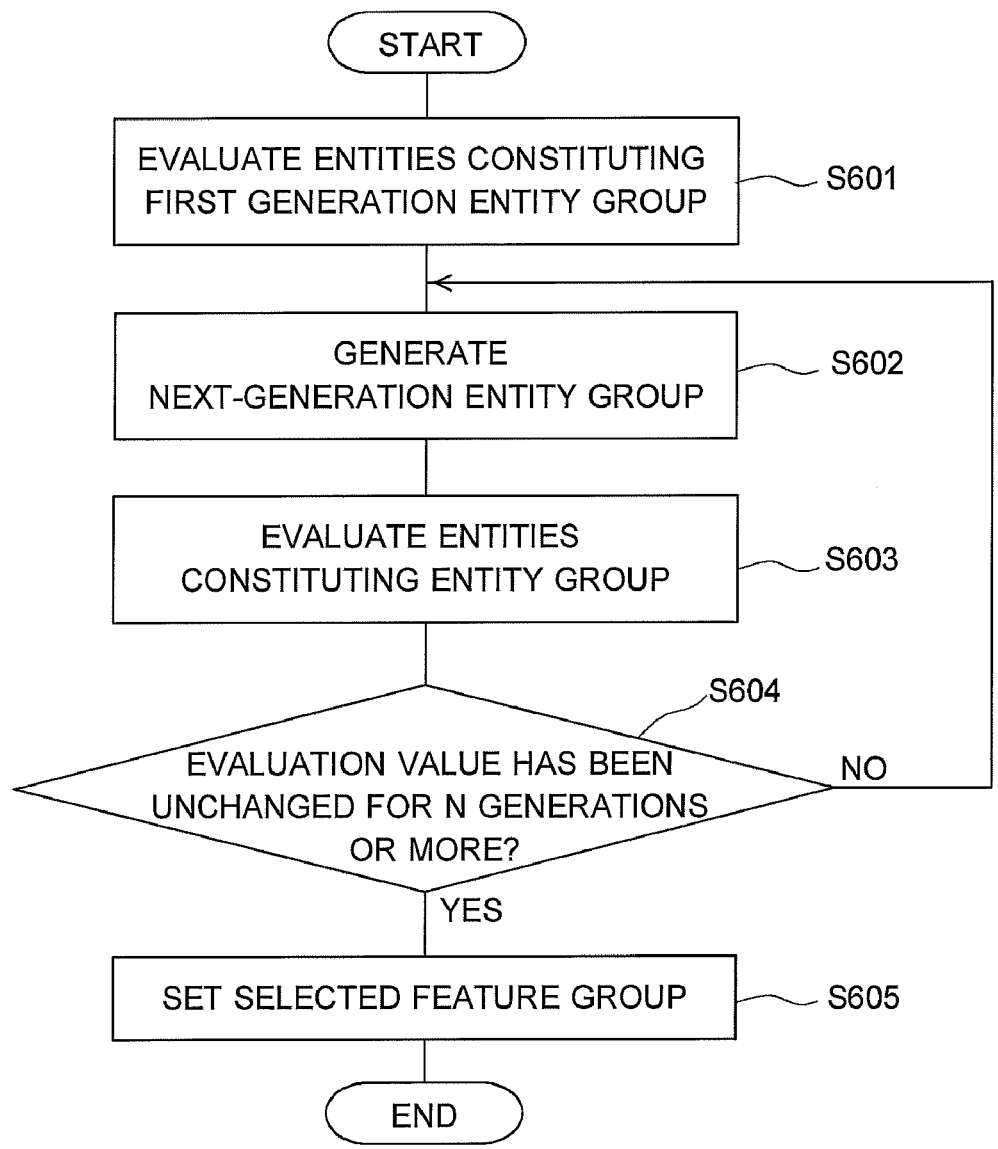
FIG. 9 is a flowchart showing a flow of operations performed by the control unit when clustering training images and selecting feature quantities based on the result of such clustering in the case in which a genetic algorithm has been employed as a combinatorial optimizing algorithm.

FIG. 9 is a flowchart showing a flow of operations performed by the control unit 41 when clustering training images and selecting feature quantities based on the result of such clustering, in the case in which a genetic algorithm has been employed as the combinatorial optimizing algorithm.

Note that in the present embodiment, the GA parameters are as follows: the crossover method is uniform crossover, the selection and generation change method was tournament selection (TS)+elite selection strategy (ESS), the size of the entity group (number of entities "P") was 100 entities, and the mutation rate was 0.01/genetic locus; however these values can be adjusted appropriately.

First, the controller 41 evaluates the entities constituting the first generation entity group (S601). In the first generation entity group, all bits of one entity are set to 1, and the genetic character of the remaining P−1 entities is determined by random numbers.

The fitness of each entity is calculated by a single instance of operation of the feature selector 41b, feature map generator 41c, and feature map evaluator 41d modules. Accordingly, the evaluation for all entities in the entity group is completed by causing the feature selector 41b, feature map generator 41c, and feature map evaluator 41d modules to operate a maximum of P times. Note that the case of an entity whose genetic locus is all zeros is an exception, and in this case, the above modules are not caused to operate, and the evaluation value is set to the minimum value (0).

Next, the controller 41 generates a next-generation entity group (S602). Here, superior entities that have a high evaluation value (referring to a feature group that is suited for evaluating the conditions of biological samples) are selected from among all entities in the entity group by TS, and thereafter the next-generation entity group is generated by the uniform crossover method. Also, the entities that have a particularly high evaluation value are preserved in the next generation (ESS). Due to employing the ESS, the maximum evaluation value either increases or is unchanged in the next generation.

Next, the control unit 41 evaluates the entities constituting the generated entity group in the same way as the case described above (S603). Then, the control unit 41 determines whether the situation in which the evaluation value is unchanged has continued for N (N being appropriately set by the user) generations or more (S604). Here, if it has been determined that such situation has not continued for N generations or more (S604:NO), the control unit 41 returns to step S602. In contrast, if it has been determined that such situation has continued for N generations or more (S604: YES), the control unit 41 stops the genetic algorithm, and sets the genetic character of the best entity at this time, that is to say, the combination of feature quantities to be selected, as the selected feature group (S605). This setting is performed by the feature selector 41b storing this feature quantity combination in the storage unit 42. Also, the feature map generator 41c generates a feature map using the combination of feature quantities pertaining to the best entity, and stores the feature map in the storage unit 42. This feature map is used in operations performed in the later-described classification mode.

The above processing results in completing the selection of a combination of feature quantities (optimum feature group) to be used in the subsequent classification mode, and the labeling of cluster names for all of the training images in accordance with the annotation.

Figure 10:
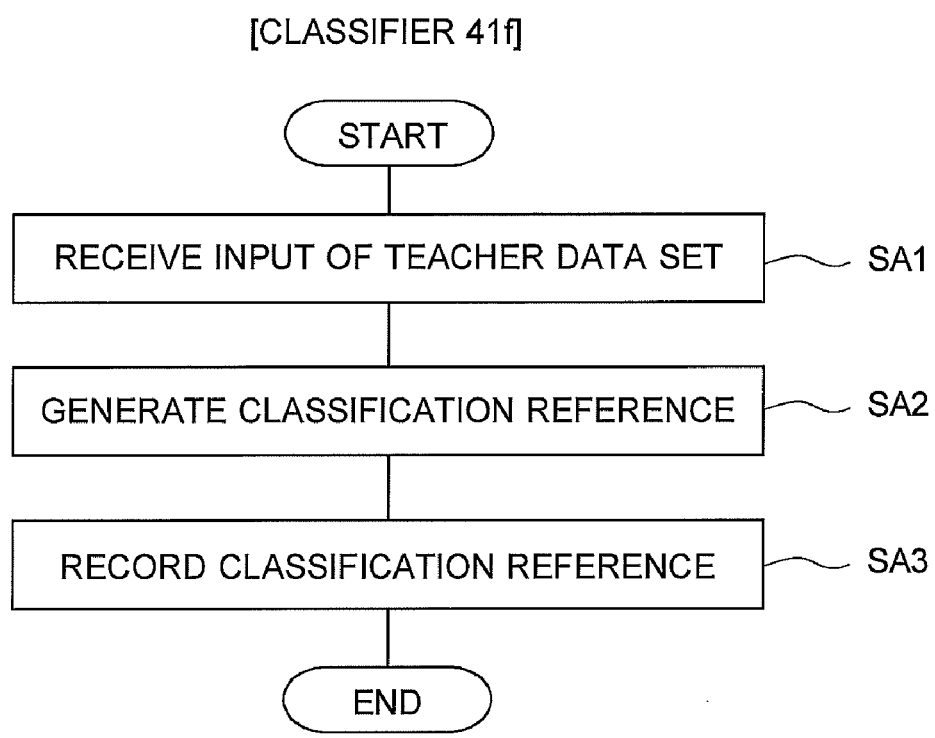
FIG. 10 is a flowchart showing a flow of operations performed by a classifier 41$f$ in the classifier generation mode.

FIG. 10 is a flowchart showing a flow of operations performed by the classifier 41f in the classifier generation mode. First, the classifier 41f receives an input of the optimum feature group from the feature selector 41b as a teacher data set (SA1), generates a classification reference for class classification based on the correspondence relationship between the class names and values (optimum feature vectors) of the optimum feature group of each training image (SA2), and records the classification reference in the storage unit 42 (SA3). A supervised learning algorithm is used in the generation of the classification reference. In the present embodiment, a support vector machine (SVM) was employed as the supervised learning algorithm. An SVM is an algorithm that determines a hyperplane, which is to be a boundary between classes, in a feature space whose number of dimensions is determined by the number of feature groups, so that the distance from feature vectors closest to the hyperplane is maximized. The generation of the classifier is completed by recording the classification reference.

Figure 15A:
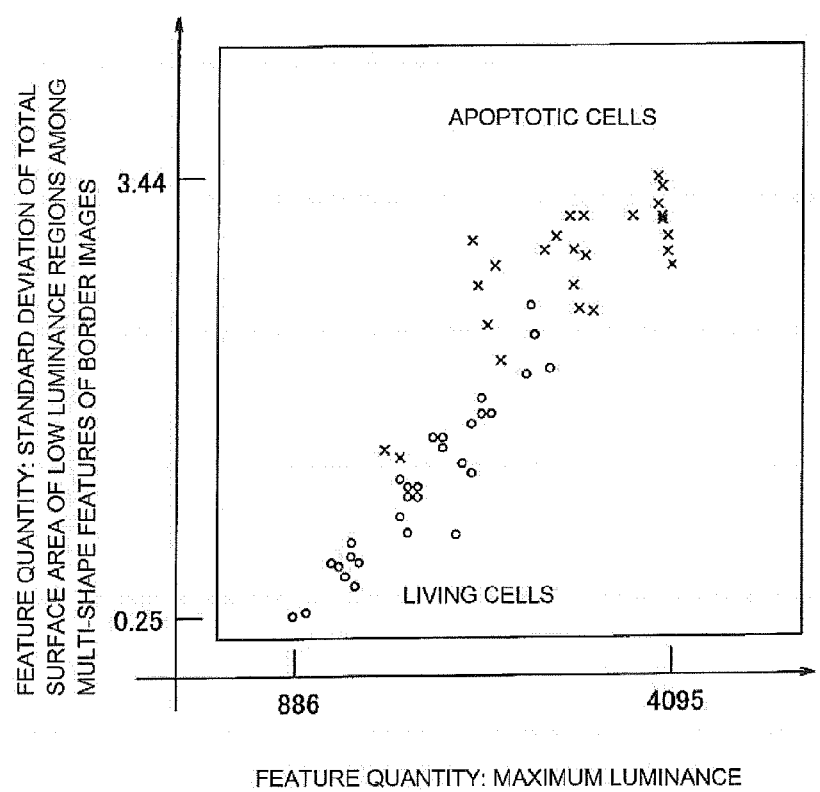
FIG. 15A is a diagram for describing an example of a classification reference generated by the classifier 41$f$ in the classifier generation mode.
Figure 15B:
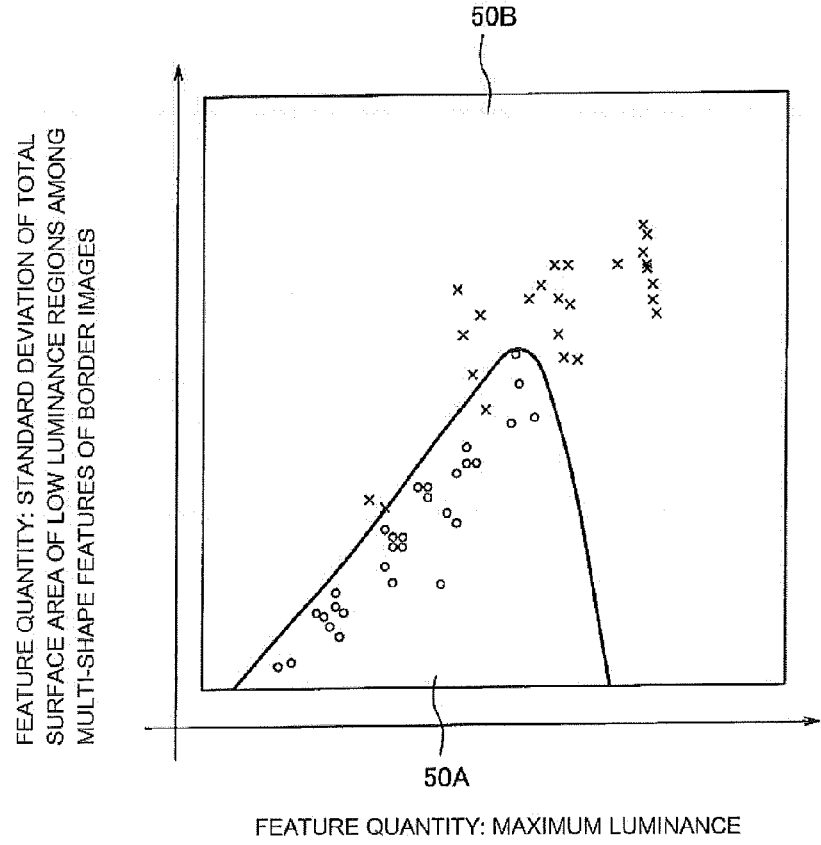
FIG. 15B is another diagram for describing an example of a classification reference generated by the classifier 41f in the classifier generation mode.

FIGS. 15A and 15B are diagrams for describing an example of a classification reference generated by the classifier 41f in the classifier generation mode. FIGS. 15A and 15B shows an example of a classification reference used in an apoptosis determination (two classes: living cell, apoptotic cell) based on fluorescence images of the nuclei and chromosomes of HeLa cells, the classification reference being a separation hyperplane generated with use of the SVM in the classifier 41f when the two feature quantities described below were selected. Note that in FIGS. 15A and 15B, one of the selected feature quantities is "maximum luminance" and corresponds to the horizontal axis, and the other selected feature quantity is "standard deviation of the total surface area of low luminance regions among the multi-shape features of the border images" and corresponds to the vertical axis.

FIG. 15A shows a distribution of training images in a feature space composed of the above two feature quantities, a separation hyperplane not having been generated yet, and the training images having been labeled with class names according to an annotation. One point corresponds to one training image. The class name of points plotted as a circle in the figure is "living cell", and the class name of points plotted as an X is "apoptotic cell".

Also, FIG. 15B shows a condition in which a separation hyperplane indicated by a solid line has been generated as the separation reference. The phase shown by reference character 50A corresponds to "living cell", and the phase shown by reference character 50B corresponds to "apoptotic cell". The classifier 41f stores the separation hyperplane and the class name of each phase in the storage unit 42.

Note that although not shown here, if there are approximately several tens of feature quantities constituting the optimum feature group, the space (feature space) in which the separation hyperplane that is the separation reference exists is a space having several tens of dimensions.

(2) Classification Mode

In the classification mode, in the classification of one image, after the processing of the feature extractor 41a has ended, the feature selector 41b, feature map generator 41c, and classifier 41f modules are each executed one time.

The flow of operations performed by the feature extractor 41a is the same as in the classifier generation mode. As shown in FIG. 4, the feature extractor 41a receives an input of images captured by the imaging apparatus 3 from the imaging apparatus 3 (S101). Hereinafter, these input images are called classification target images. Next, the feature extractor 41a extracts a plurality of feature quantities that the input images have (S102), and outputs the extracted feature quantities to the feature selector 41b as feature groups (S103).

Next, the feature selector 41b reads, from the storage unit 42, the feature group ultimately selected in the classifier generation mode as the optimum feature group, selects an optimum feature group from among the feature groups input from the feature extractor 41a, and outputs these to the feature map generator 41c and the classifier 41f. Thereafter, the feature map generator 41c and the classifier 41f execute the following processing.

Figure 13:
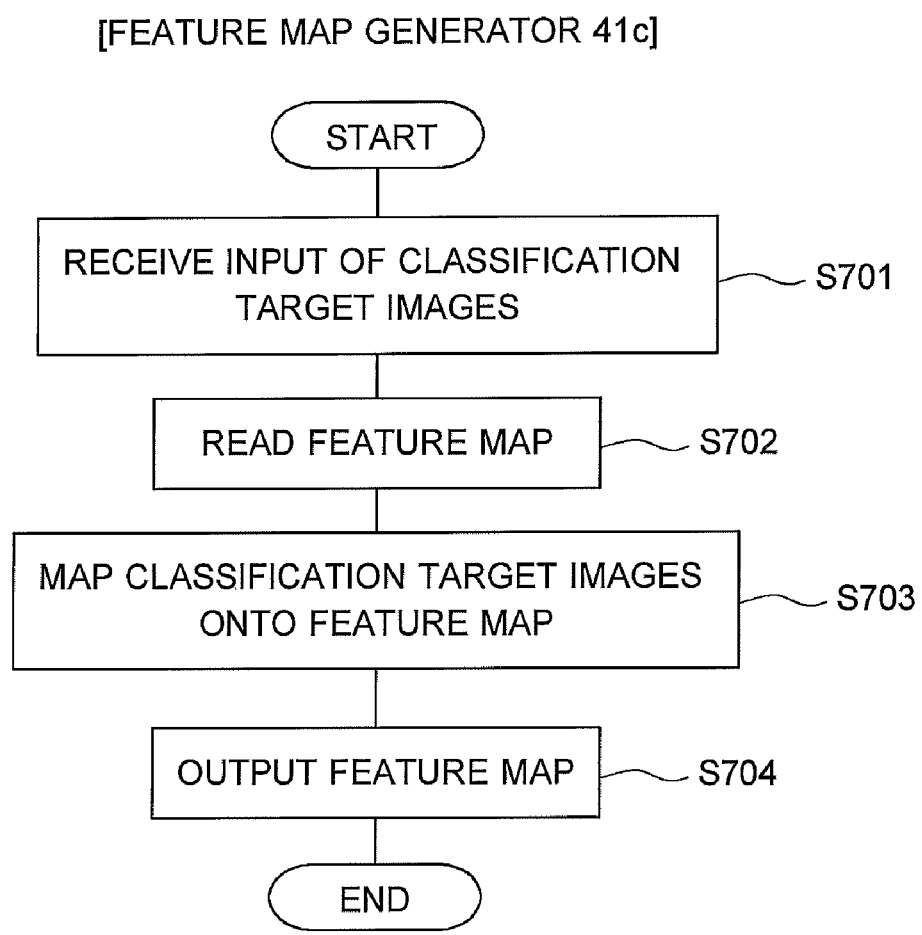
FIG. 13 is a flowchart showing a flow of operations performed by the feature map generator in a classification mode.

FIG. 13 is a flowchart showing a flow of operations performed by the feature map generator 41c in the classification mode. The feature map generator 41c receives an input of classification target images, which are images targeted for image classification (S701). Next, the feature map generator 41c reads the feature map stored in the storage unit 42, that is to say, the feature map that has been generated based on the optimum feature group selected in the classifier generation mode (S702).

Then, the feature map generator 41c maps the classification target images on the read feature map with use of the optimum feature group input from the feature selector 41b (S703), and outputs the feature map on which mapping has been performed to the output apparatus 5 (S704). The output apparatus 5 displays the feature map input from the feature map generator 41c on the screen. This feature map can be said to illustrate which images in the training image group each classification target image is similar to.

Figure 14:
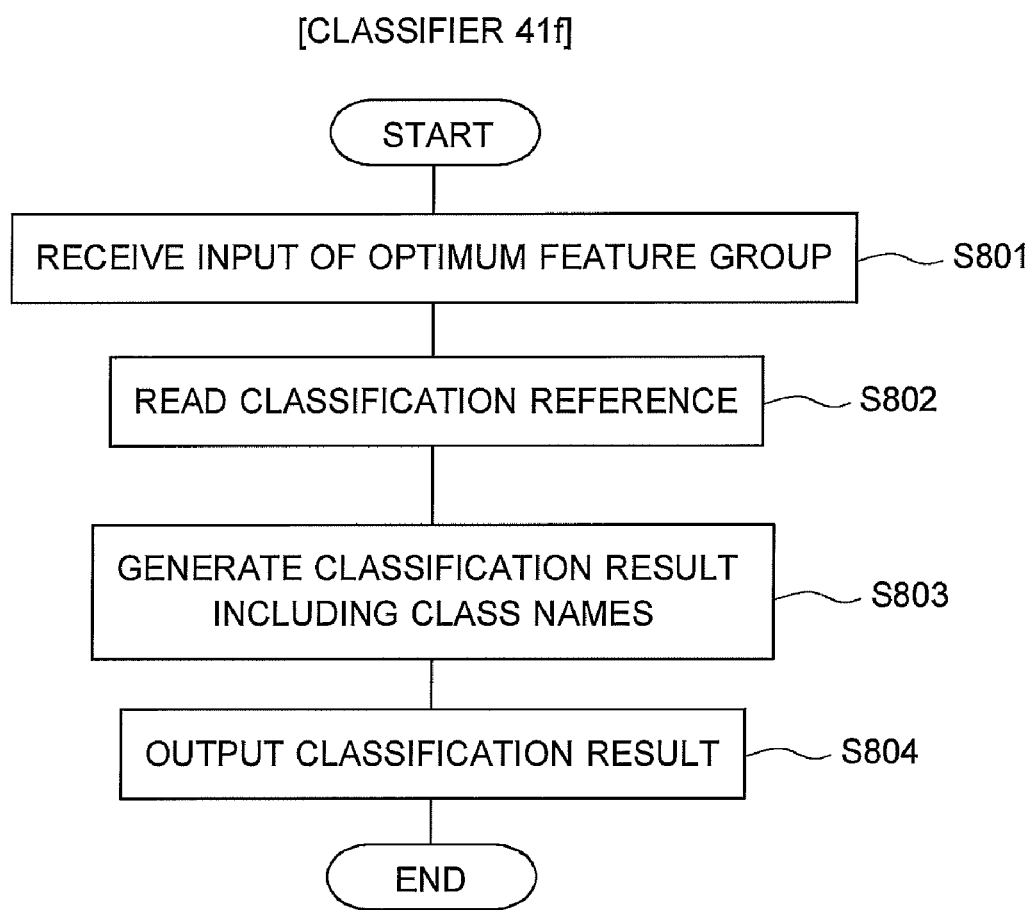
FIG. 14 is a flowchart showing a flow of operations performed by the classifier in the classification mode.

FIG. 14 is a flowchart showing a flow of operations performed by the classifier 41f in the classification mode. The classifier 41f receives an input of the optimum feature group from the feature selector 41b (S801), reads the classification reference from the storage unit 42 (S802), classifies the values in the optimum feature group based on the classification reference and generates a classification result including class names indicating the conditions of biological samples (S803), and outputs the classification result to the output apparatus 5 (S804). The output apparatus 5 displays the classification result input from the classifier 41f on the screen.

In this way, by referencing the feature map and classification result displayed on the screen of the output apparatus 5, the user can check the result of the classification of the classification target images.

Although the above describes the case in which the present invention has been applied to an image classification system that classifies captured fluorescence images of cells, the present invention is not limited to this, and instead can be applied to image classification systems that classify images acquired by various types of imaging apparatuses. For example, the present invention can be applied to an image classification system for a medical application, and in this case, examples of the captured images include microscope images, X-ray images, MRI images (nuclear magnetic resonance images), and ultrasound images that show, for example, biological entities, biological tissue, sections of biological entities or tissue, biological entity-derived biological fluid such as blood, and cells.

WORKING EXAMPLES

The following describes Working Examples 1 to 6 in which cells were classified using the image classification system of the embodiment described above. Table 4 shows the determination accuracy in each working example.

images, and it was determined which of six classes, namely G2 phase, prophase-prometaphase, metaphase, anaphase-telophase, cytokinesis, and G1 phase, the images belong to. As shown in Table 4, when the detection result in the present working example was compared with the visual results, the detection accuracy was 90.9%.

TABLE 4

| Working Example | Determination content | Determination accuracy (%) |
|---|---|---|
| Working Example 1 | Cell cycle phase determination from bright field images (time-series images) of HeLa cells (6 classes: $G_2$ phase, prophase-prometaphase, metaphase, anaphase-telophase, cytokinesis, $G_1$ phase) | 90.9 |
| Working Example 2 | Apoptosis determination from bright field images of HeLa cells (2 classes: living cell, apoptotic cell) | 96.9 |
| Working Example 3 | Cell cycle phase determination from fluorescence images of nuclei and chromosomes of HeLa cells (8 classes: $G_2$ phase, prophase, prometaphase, metaphase, anaphase, telophase, cytokinesis, $G_1$ phase) | 88.1 |
| Working Example 4 | Cell cycle phase determination from fluorescence images (time-series images) of nuclei and chromosomes of HeLa cells (8 classes: $G_2$ phase, prophase, prometaphase, metaphase, anaphase, telophase, cytokinesis, $G_1$ phase) | 95.2 |
| Working Example 5 | Apoptosis determination from fluorescence images (time-series images) of nuclei and chromosomes of HeLa cells (2 classes: living cell, apoptotic cell) | 95.1 |
| Working Example 6 | Cell type determination from bright field images of epidermal tissue of *Arabidopsis thaliana* leaf (2 classes: epidermal cell, guard cell) | 97.9 |

Working Example 1

In Working Example 1, class (stage) determination was performed with respect to the cell cycle phases of HeLa cells. Bright field images (time-series images) of HeLa cells were used as the training images and the classification target

Working Example 2

In Working Example 2, an apoptosis determination was performed on HeLa cells. Bright field images of HeLa cells were used as the training images and the classification target images, and it was determined whether each HeLa cell was a living cell or an apoptotic cell. Table 5 shows feature groups extracted by the feature extractor 41a in the classifier generation mode.

TABLE 5

Feature quantities and optimum feature groups of Working Example 2
(apoptosis determination from bright field images of HeLa cells)

| Broad classification of feature quantities | Intermediate classification of feature quantities | Detailed classification of feature quantities | Feature quantities |
|---|---|---|---|
| Grayscale image | Shape feature | Feature of overall shape | Surface area, (perimeter), circularity, major axis length, minor axis length, major axis to minor axis ratio, complexity |
| | | Feature of individual shapes | Average surface area, average perimeter, average of major axis to minor axis ratio, average circularity |
| | | Luminance distribution feature within a shape | Average, median, standard deviation, skewness, kurtosis |
| | Texture feature | Luminance distribution feature of overall image | Minimum value, (maximum value), spread, (average), median, (difference between average and median), (standard deviation), (standard deviation/spread), skewness, kurtosis |
| | | Gray-level co-occurrence matrix (GLCM) | Homogeneity, contrast, standard deviation, average, entropy, skewness |
| | | Multi-shape feature | Distribution of number of individual shapes in high luminance regions: (maximum value), (average), (luminance yielding average), median, standard deviation |
| | | | Distribution of number of individual shapes in low luminance regions: maximum value, average, luminance yielding average, median, standard deviation |
| | | | Distribution of complexity in high luminance regions: (maximum value), (average), luminance yielding average, median, standard deviation |
| | | | Distribution of complexity in low luminance regions: (maximum value), average, luminance yielding average, median, standard deviation |
| | | | Distribution of displacement in high luminance regions: maximum value, (average), luminance yielding average, median, standard deviation |
| | | | Distribution of displacement in low luminance regions: maximum value, average, luminance yielding average, median, standard deviation |
| | | | Distribution of inertia moment in high luminance regions: maximum value, average, luminance |

TABLE 5-continued

Feature quantities and optimum feature groups of Working Example 2
(apoptosis determination from bright field images of HeLa cells)

| Broad classification of feature quantities | Intermediate classification of feature quantities | Detailed classification of feature quantities | Feature quantities |
|---|---|---|---|
| | | | yielding average, median, standard deviation |
| | | | Distribution of inertia moment in low luminance regions: maximum value, average, luminance yielding average, median, standard deviation |
| | | | Distribution of total surface area in high luminance regions: maximum value, average, luminance yielding average, median, standard deviation |
| | | | Distribution of total surface area in low luminance regions: maximum value, average, luminance yielding average, median, standard deviation |
| | | | Distribution of average surface area in high luminance regions: maximum value, average, luminance yielding average, median, standard deviation |
| | | | Distribution of average surface area in low luminance regions: maximum value, average, luminance yielding average, median, standard deviation |
| Boundary image | Shape feature | Feature of overall shape | (Surface area), (perimeter), circularity, major axis length, minor axis length, major axis to minor axis ratio, complexity |
| | | Feature of individual shapes | Average surface area, average perimeter, average of major axis to minor axis ratio, average circularity |
| | | Luminance distribution feature within a shape | Average, median, (standard deviation), skewness, kurtosis |
| | Texture feature | Luminance distribution feature of overall image | Minimum value, maximum value, spread, average, median, difference between average and median, standard deviation, standard deviation/spread, skewness, kurtosis |
| | | Gray-level co-occurrence matrix (GLCM) | Homogeneity, contrast, standard deviation, average, entropy, skewness |
| | | Multi-shape feature | Distribution of number of individual shapes in high luminance regions: (maximum value), (average), luminance yielding average, median, standard deviation |
| | | | Distribution of number of individual shapes in low luminance regions: maximum value, average, luminance yielding average, median, standard deviation |
| | | | Distribution of complexity in high luminance regions: (maximum value), (average), luminance yielding average, median, standard deviation |
| | | | Distribution of complexity in low luminance regions: maximum value, average, luminance yielding average, median, standard deviation |
| | | | Distribution of displacement in high luminance regions: maximum value, average, luminance yielding average, median, standard deviation |
| | | | Distribution of displacement in low luminance regions: maximum value, average, luminance yielding average, median, standard deviation |
| | | | Distribution of inertia moment in high luminance regions: maximum value, average, luminance yielding average, median, standard deviation |
| | | | Distribution of inertia moment in low luminance regions: (maximum value), average, luminance yielding average, median, standard deviation |
| | | | Distribution of total surface area in high luminance regions: maximum value, average, luminance yielding average, median, standard deviation |
| | | | Distribution of total surface area in low luminance regions: (maximum value), (average), luminance yielding average, median, standard deviation |
| | | | Distribution of average surface area in high luminance regions: (maximum value), (average), luminance yielding average, median, standard deviation |
| | | | Distribution of average surface area in low luminance regions: maximum value, average, luminance yielding average, median, standard deviation |

In Table 5, the feature quantities inside parentheses are feature quantities selected as the optimum feature group. As shown in Table 4, when the detection result in the present working example was compared with the visual results, the detection accuracy was 96.9%.

Working Example 3

In Working Example 3, class (stage) determination was performed with respect to the cell cycle phases of HeLa cells. Fluorescence images of the nuclei and chromosomes of HeLa cells were used as the training images and the classification target images, and it was determined which of eight classes, namely G2 phase, prophase, prometaphase, metaphase, anaphase, telophase, cytokinesis, and G1 phase, the images belong to. As shown in Table 4, when the detection result in the present working example was compared with the visual results, the detection accuracy was 88.1%.

Working Example 4

In Working Example 4, class (stage) determination was performed with respect to the cell cycle phases of HeLa cells. Fluorescence images (time-series images) of the nuclei and chromosomes of HeLa cells were used as the training images and the classification target images, and it was determined which of eight classes, namely G2 phase, prophase, prometaphase, metaphase, anaphase, telophase, cytokinesis, and G1 phase, the images belong to. As shown in Table 4, when the detection result in the present working example was compared with the visual results, the detection accuracy was 95.2%.

Working Example 5

In Working Example 5, an apoptosis determination was performed on HeLa cells. Fluorescence images (time-series images) of the nuclei and chromosomes of HeLa cells were used as the training images and the classification target images, and it was determined whether each HeLa cell was a living cell or an apoptotic cell. Table 6 shows feature groups extracted by the feature extractor 41a in the classifier generation mode.

TABLE 6

Feature quantities extracted by feature extractor

| Broad classification of feature quantities | Intermediate classification of feature quantities | Detailed classification of feature quantities | Feature quantities |
|---|---|---|---|
| Grayscale image | Shape feature | Feature of overall shape | (Surface area), perimeter, circularity, major axis length, minor axis length, major axis to minor axis ratio, complexity |
| | | Feature of individual shapes | (Average surface area), average perimeter, average of major axis to minor axis ratio, average circularity |
| | | Luminance distribution feature within a shape | (Average), median, (standard deviation), skewness, kurtosis |
| | Texture feature | Luminance distribution feature of overall image | Minimum value, (maximum value), (spread), (average), median, (difference between average and median), (standard deviation), standard deviation/spread, skewness, kurtosis |
| | | Gray-level co-occurrence matrix (GLCM) | Homogeneity, contrast, standard deviation, average, entropy, skewness |
| | | Multi-shape feature | Distribution of number of individual shapes in high luminance regions: maximum value, average, luminance yielding average, median, standard deviation |
| | | | Distribution of number of individual shapes in low luminance regions: maximum value, average, luminance yielding average, median, standard deviation |
| | | | Distribution of complexity in high luminance regions: maximum value, average, luminance yielding average, median, standard deviation |
| | | | Distribution of complexity in low luminance regions: maximum value, average, luminance yielding average, median, standard deviation |
| | | | Distribution of displacement in high luminance regions: maximum value, (average), luminance yielding average, median, standard deviation |
| | | | Distribution of displacement in low luminance regions: maximum value, average, luminance yielding average, median, standard deviation |
| | | | Distribution of inertia moment in high luminance regions: maximum value, average, luminance yielding average, median, standard deviation |
| | | | Distribution of inertia moment in low luminance regions: maximum value, average, luminance yielding average, median, standard deviation |
| | | | Distribution of total surface area in high luminance regions: maximum value, (average), (luminance yielding average), median, standard deviation |
| | | | Distribution of total surface area in low luminance regions: maximum value, (average), (luminance yielding average), median, (standard deviation) |
| | | | Distribution of average surface area in high luminance regions: maximum value, average, luminance yielding average, median, standard deviation |
| | | | Distribution of average surface area in low luminance regions: maximum value, average, luminance yielding average, median, standard deviation |
| Boundary image | Shape feature | Feature of overall shape | Surface area, perimeter, circularity, major axis length, minor axis length, major axis to minor axis ratio, complexity |
| | | Feature of individual shapes | Average surface area, average perimeter, average of major axis to minor axis ratio, average circularity |
| | | Luminance distribution feature within a shape | (Average), median, (standard deviation), skewness, kurtosis |
| | Texture feature | Luminance distribution feature of overall image | Minimum value, maximum value, spread, average, median, difference between average and median, standard deviation, standard deviation/spread, skewness, kurtosis |
| | | Gray-level co-occurrence matrix (GLCM) | Homogeneity, contrast, standard deviation, average, entropy, skewness |
| | | Multi-shape feature | Distribution of number of individual shapes in high luminance regions: maximum value, average, luminance yielding average, median, standard deviation |
| | | | Distribution of number of individual shapes in low luminance regions: (maximum value), average, luminance yielding average, median, standard deviation |
| | | | Distribution of complexity in high luminance regions: (maximum value), average, luminance yielding average, median, standard deviation |
| | | | Distribution of complexity in low luminance regions: maximum value, average, luminance yielding average, median, (standard deviation) |
| | | | Distribution of displacement in high luminance regions: maximum value, average, luminance yielding average, median, (standard deviation) |
| | | | Distribution of displacement in low luminance regions: maximum value, (average), luminance yielding average, median, standard deviation |
| | | | Distribution of inertia moment in high luminance regions: maximum value, average, (luminance yielding average), median, standard deviation |
| | | | Distribution of inertia moment in low luminance regions: maximum value, average, luminance yielding average, median, (standard deviation) |
| | | | Distribution of total surface area in high luminance regions: maximum value, average, luminance yielding average, median, standard deviation |
| | | | Distribution of total surface area in low luminance regions: maximum value, average, luminance yielding average, median, (standard deviation) |
| | | | Distribution of average surface area in high luminance regions: maximum value, average, luminance yielding average, median, (standard deviation) |
| | | | Distribution of average surface area in low luminance regions: maximum value, average, luminance yielding average, median, (standard deviation) |

In Table 6, the feature quantities inside parentheses are feature quantities selected as the optimum feature group. As shown in Table 4, when the detection result in the present working example was compared with the visual results, the detection accuracy was 95.1%.

Figure 16A:
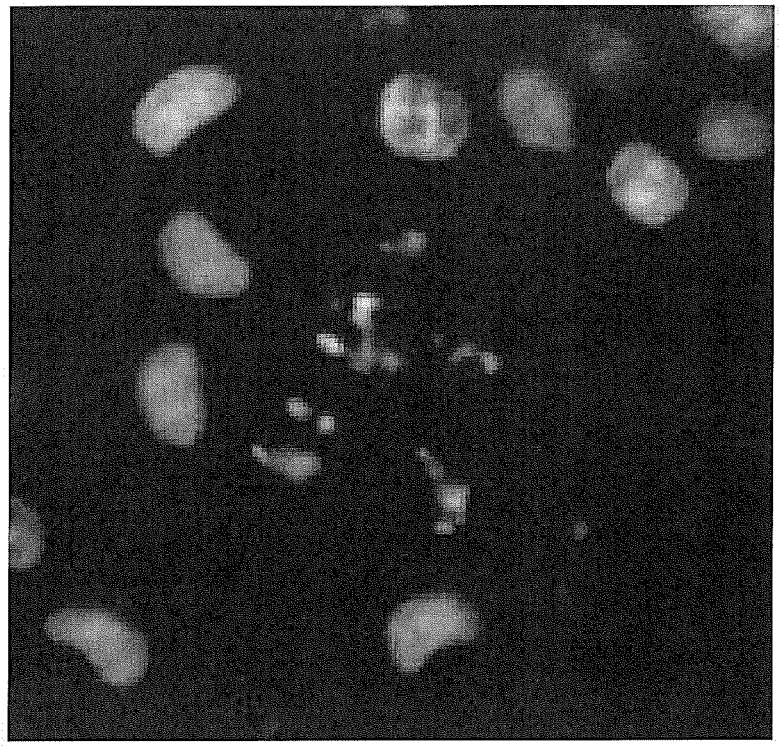
FIG. 16A is a screen displayed by the output apparatus showing an input image in Working Example 5.
Figure 16B:
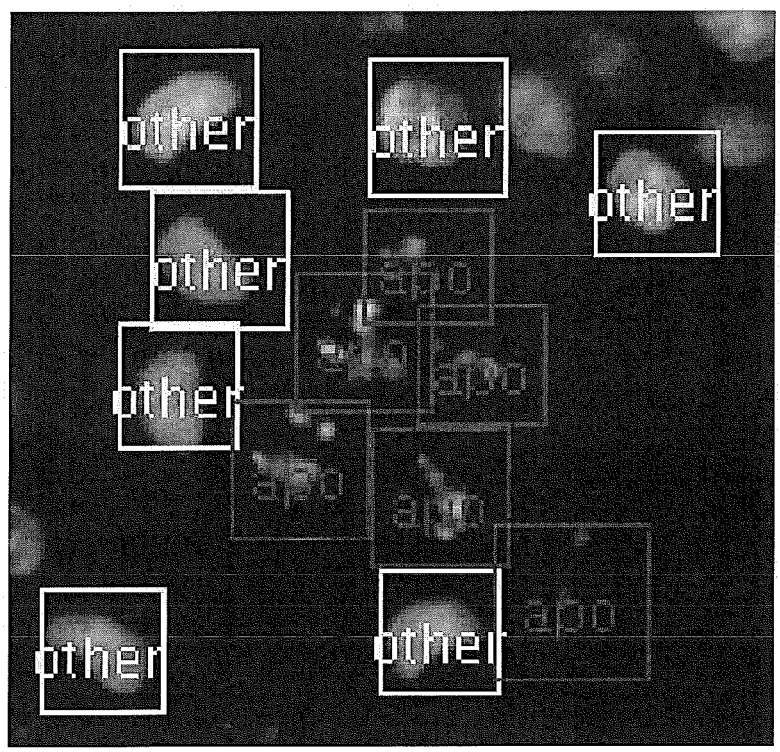
FIG. 16B is a screen displayed by the output apparatus showing measurement results.

FIG. 16A shows a screen displayed by the output apparatus 5 showing an input image in the present working example. While watching the screen shown in FIG. 16A and another screen showing the input image, the input apparatus 6 was operated, and a plurality of regions including the nuclei and chromosomes of the HeLa cells were selected as the classification target images. Determination was performed on the selected classification target images in the classification mode, and the determination result was displayed by the output apparatus 5. FIG. 16B shows a screen displayed by the output apparatus 5 showing the detection result of the present working example. In FIG. 16B, the regions enclosed in rectangles are the selected classification target images, the notation "other" indicates classification target images determined to be "living cells", and the notation "apo" indicates classification target images determined to be "apoptotic cells". The determination result for the classification target images shown in FIG. 16B was exactly the same as the visual result.

Working Example 6

In Working Example 6, the cell types of epidermal tissue of an *Arabidopsis thaliana* leaf were determined. Bright field images of the epidermal tissue of an *Arabidopsis thaliana* leaf were used as the training images and the classification target images, and whether cells were epidermal cells or guard cells was determined. As shown in Table 4, when the detection result in the present working example was compared with the visual results, the detection accuracy was 97.9%.

As described above, in the working examples, cells were classified with a very high detection accuracy.

Note that as with the above-described working examples, in the case of classifying images of biological samples, there are many cases in which the classification reference does not exist as an external reference. Even if the classification guidelines have been given empirically, such guidelines are almost always neither obvious nor consistent enough to be implemented as a computer program for automating the classification. Furthermore, in the classification of images of biological samples, there are often cases in which clear boundaries do not exist, such as the case of classifying images of cells into the various phases of the cell cycle, and therefore phases are conveniently classified in order to describe life phenomenon. In the case of such a classification target, it is not only necessary to simply determine the classification reference, but it is also necessary to examine the classification guidelines, that is to say, into how many types of classes and into which of such classes input image groups are to be classified. In the present invention, not only is image classification automated, but also clustering is performed and an image group distribution condition is visualized prior to the determination of the classification reference, thus assisting the user in the process of determining the guidelines of into how many types of classes and into which of such classes the image groups are to be classified.

Also, in many biological sample images, the nature of the sample cannot be sufficiently expressed by merely shape feature quantities, and therefore when classifying such images it is necessary to rely on texture feature quantities that express the texture and pattern of images. However, there are several hundred or more types of texture feature quantities, which is many more than the types of shape feature quantities.

Only a small portion of the many texture feature quantities is useful to image classification, and furthermore the texture feature quantities that are suitable differs depending on the type and nature of the images, and on the classification purpose. For this reason, in the development of biological sample image classification systems, it has been common to go through a step of selecting feature quantities suited for classification from among a large number of texture feature quantities. This step can be automated by the feature group selection method realized by the present invention, therefore enabling resolving one of the main obstacles in the development of biological sample image classification systems.

Other Embodiments

The imaging apparatus 3, the image classification apparatus 4, the output apparatus 5, and the input apparatus 6 in the embodiment described above may be provided dispersed on a network. Also, whether any of the functions of the modules 41a to 41f that constitute the image classification apparatus 4 are provided by a dedicated circuit, or any of such functions are executed by a single independent computer may be changed appropriately. For example, in order to realize a remote image diagnosis system in a medical field, by providing the feature map generator 41c and feature map evaluator 41d, the output apparatus 5, and the input apparatus 6 at a site that is separated from the other apparatuses, it is possible to implement the classification target image imaging step and the annotation step performed by a specialist simultaneously and in parallel at different locations.

In this way, the present invention is applicable to a diagnosis system in a medical field, such as an MRI (nuclear magnetic resonance apparatus), a CT scan, a PET (positron emission tomography), and an X-ray fluoroscope image apparatus.

Also, although an optimum feature group is determined with use of a genetic algorithm in the above embodiment, the optimum feature group may be determined by another technique. Examples of other techniques that may be used include a local search method in which an optimum solution is obtained by a neighborhood search, a random multi-start local search method, and a tabu search method or an annealing method that improves on the localized search method.

Other Embodiments of Annotation Step

Although the annotation step is implemented in the above embodiment by the user instructing which regions in a feature map correspond to which conditions, the annotation step is not limited to this embodiment. For example, the annotation step may be implemented by annotating a portion of training images among the training images shown on the feature map. The following describes an example of such an annotation step.

First, the user selects a plurality of images from the feature map displayed on the screen of the output apparatus 5. Then, the user inputs, with use of the input apparatus 6, which group each image belongs to (e.g., image A and image B belong to group P, and image C and image D belong to group Q), thus implementing the annotation step.

In this case, the feature map evaluator 41d calculates the evaluation value of the feature map using the following Expression 2, based on teacher data obtained through the annotation.

Expression 2

$$\sum_{i=1}^{n} (\text{number of images in group } i \times \text{evaluation value in group } i)$$

Expression 2

Here, "n" indicates the number of groups. Also, "evaluation value in group" is obtained by calculation using various types of methods, such as, if there are two images, being calculated according to "1/(inter-image distance in feature map)", and if there are three or more images, being calculated according to "1/(polygonal perimeter in feature map)". Note that "polygon" in this case refers to the smallest convex polygon that contains all points where images in the same group are located in the feature map.

The following describes an example in which a fluorescence microscope was used to capture a fluorescence image of the chromosomes and nuclei of a plurality of HeLa cells in various cell phase conditions (the chromosomes and nuclei having been labeled by the introduction of a GFP-histone fusion gene), and image classification according to the present embodiment was performed using the thus-obtained captured image.

Figure 17A:
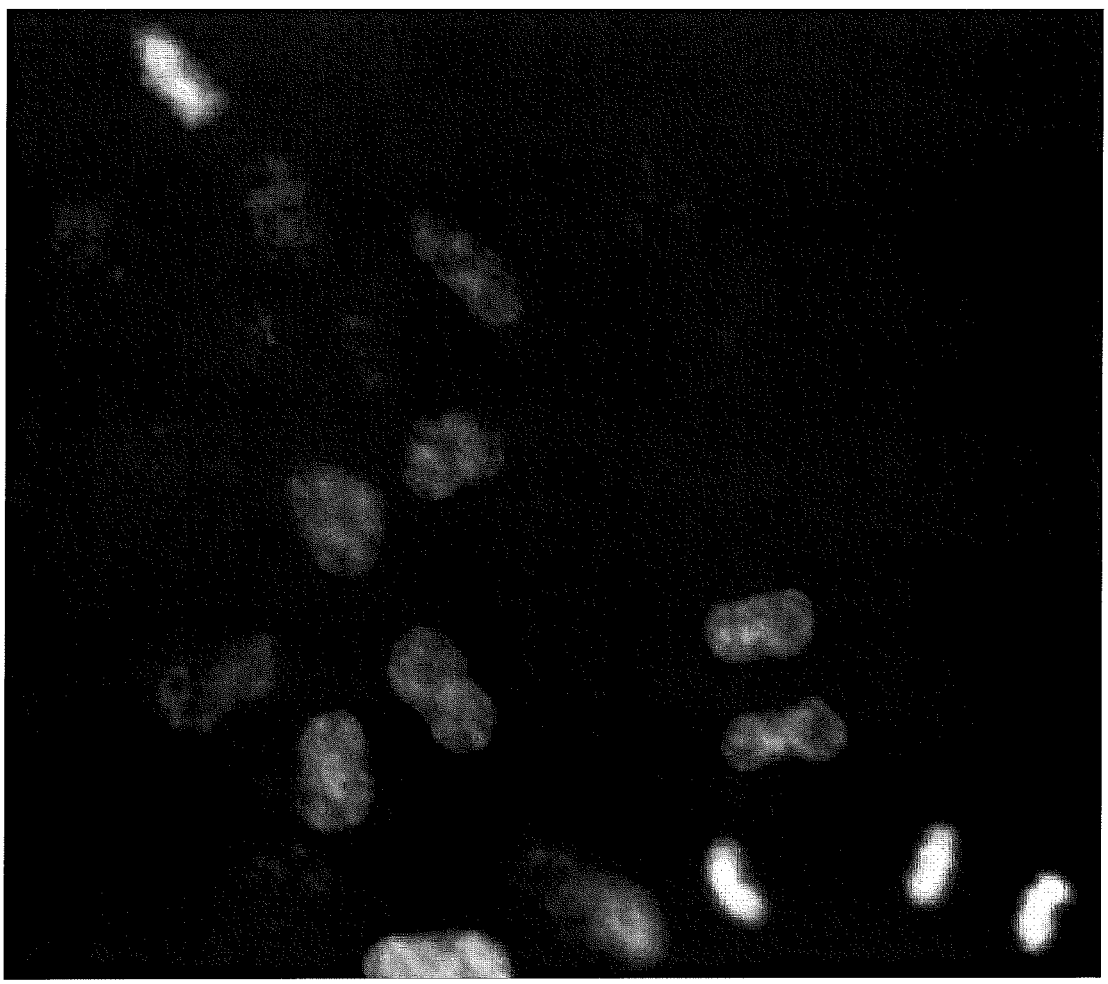
FIG. 17A is a diagram showing a partial region of a captured image.
Figure 17B:
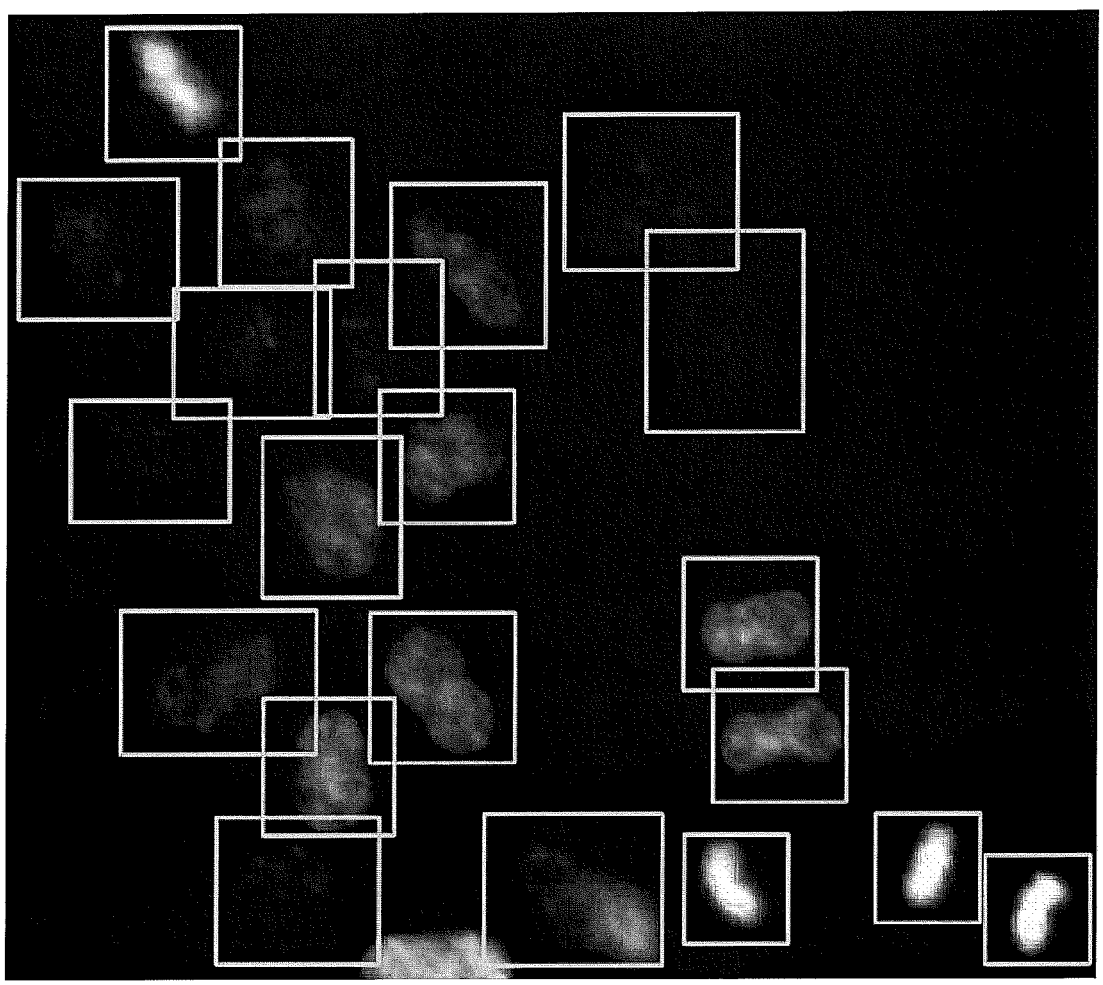
FIG. 17B is a diagram showing an example in which a rectangular region has been set around each cell in the captured image shown in FIG. 17A.

FIG. 17A is a diagram showing a partial region of the captured image. Also, FIG. 17B is a diagram showing an example in which a rectangular region has been set around each cell in the captured image shown in FIG. 17A. The rectangular regions set in this way are the training images.

Figure 18A:
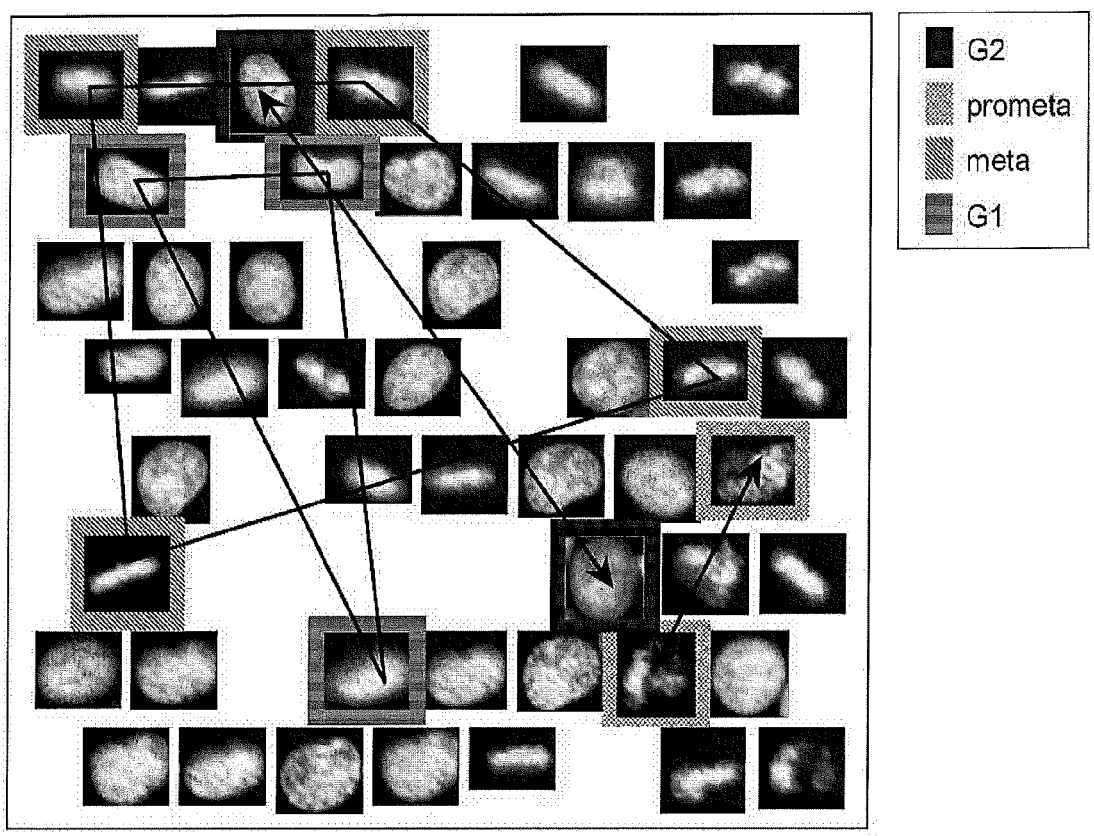
FIG. 18A is a diagram showing an example in which a specialist has annotated a feature map obtained by initial clustering executed in the classifier generation mode.

FIG. 18A is a diagram showing an example in which a specialist has annotated a feature map obtained by initial clustering executed in the classifier generation mode. Here, as shown in FIG. 18A, a total of 11 training images were targeted for annotation, and it has been determined that two of the training images belong to the G2 phase (G2), another two of the training images belong to the prometaphase (prometa), another four of the training images belong to the metaphase (meta), and the other three of the training images belong to the G1 phase (G1). As described above, for each of these four groups (cell cycle phases), if there are two images, the evaluation value in the group is calculated according to "1/(inter-image distance in feature map)", and if there are three or more images, the evaluation value in the group is calculated according to "1/(polygonal perimeter in feature map)", and the evaluation value of the feature map is calculated according to the above Expression 2 with use of the evaluation value in the group.

Figure 18B:
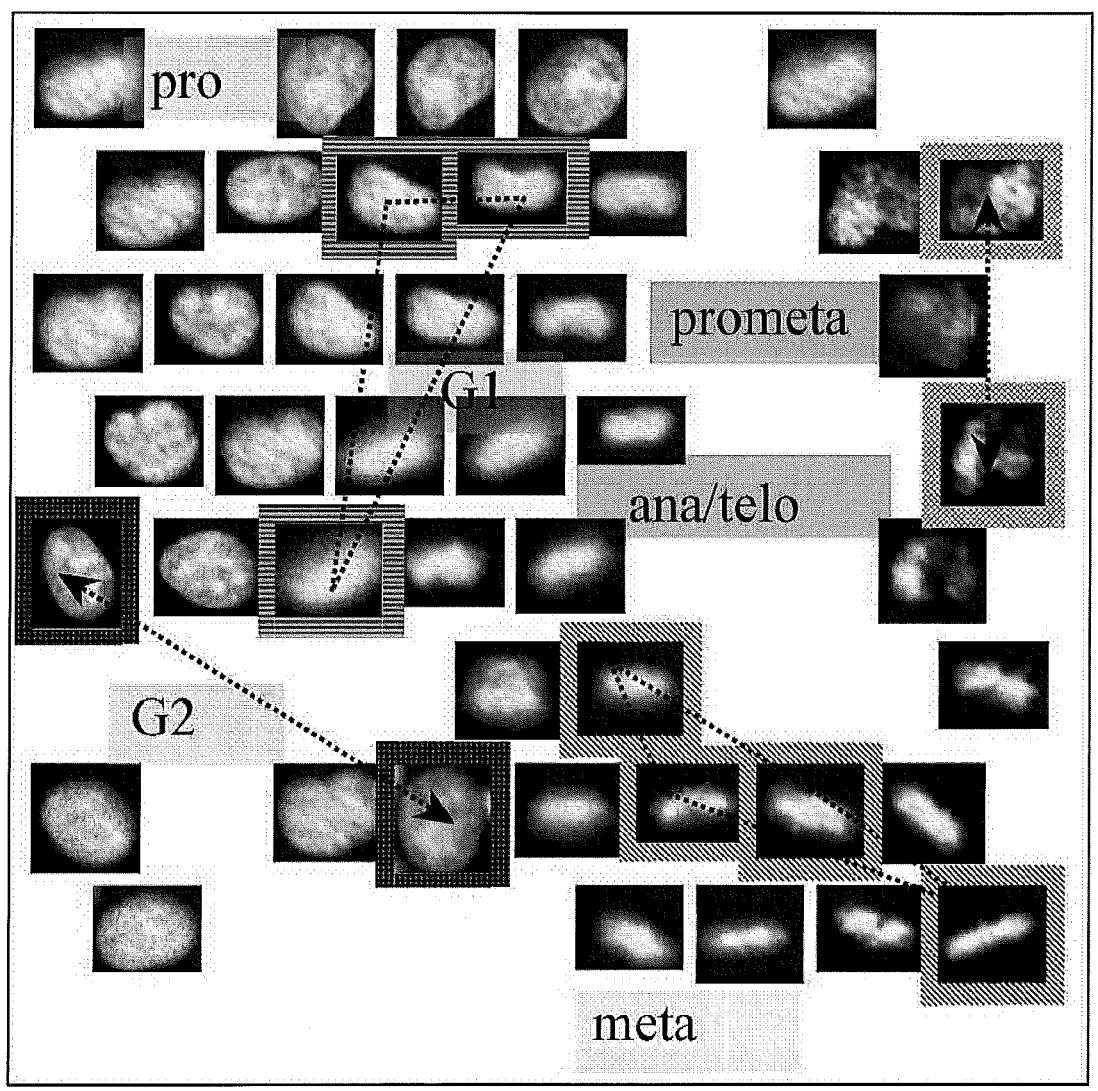
FIG. 18B is a diagram showing a feature map obtained as a result of applying a genetic algorithm.

FIG. 18B is a diagram showing a feature map obtained as a result of applying a genetic algorithm so as to obtain a high feature map evaluation value calculated as described above. Referencing FIG. 18B enables confirming that, with respect to the annotated training images, training images that belong to the same group are gathered closely together. Also, it can be confirmed that images that have not been annotated and are in the same cell cycle phases as the groups are also gathered closely together. Furthermore, it can also be confirmed that images belonging to the prophase (pro) and anaphase/telophase (ana/telo) cell cycle phases that are not targets of annotation are gathered at different sites from the G2 phase (G2), metaphase (meta), and prometaphase (prometa) groups that were targets of annotation.

Figure 19:
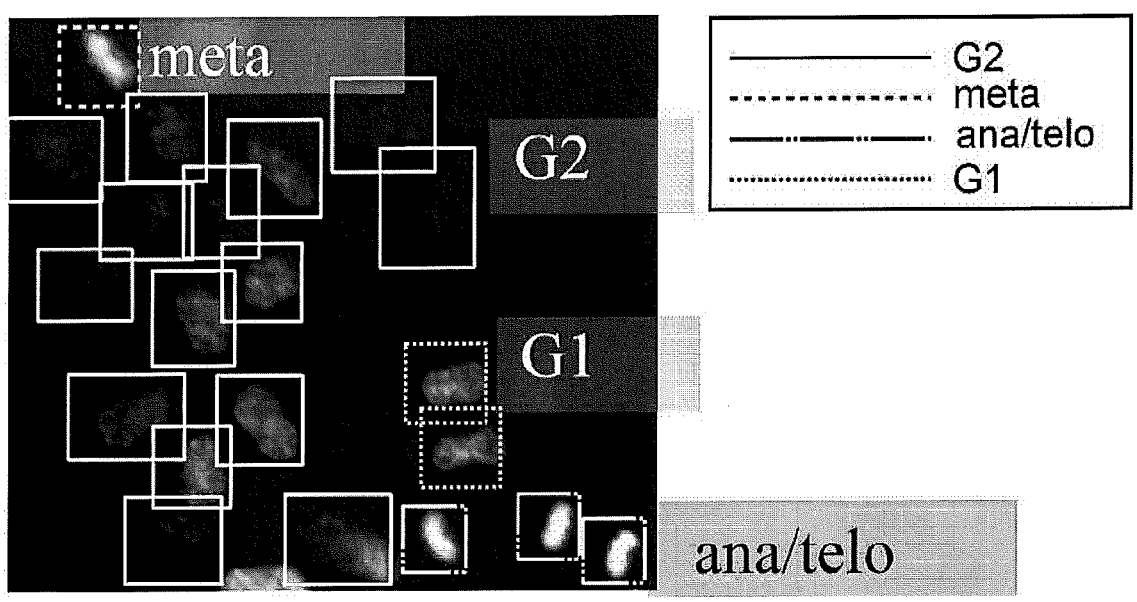
FIG. 19 is a diagram showing an execution result in the classification mode.

A classifier was generated by supervised learning based on a selected pattern of feature quantities obtained in this way, and thereafter, in the classification mode, the rectangular images regions that had not been annotated were automatically classified into cell cycle phases. FIG. 19 shows the result of this. When such results were compared to the visual results, the detection accuracy was 95.6%.

Omission of Annotation Step

As described above, in the above embodiment, in the classifier generation mode, it is possible to omit the annotation step in the initial instance of operation of the feature map evaluator 41d if the training image group is a plurality of time-series images. However, if the training images are time-series images, the omission of the annotation step is not limited to only the initial instance of operation. The following describes an example of such a case of omitting the annotation step.

Figure 20:
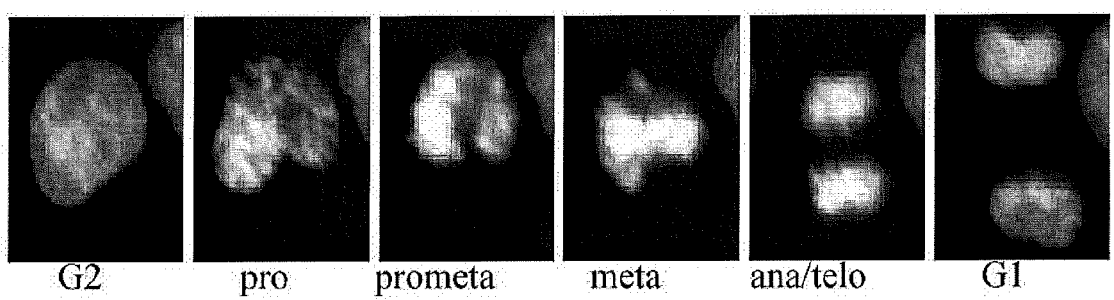
FIG. 20 is a diagram showing a plurality of time-series images that have consecutively captured each process in the cellular division of an HeLa cell.

Note that in this example, a fluorescence microscope was used to successively capture fluorescence images of the chromosome and nucleus of a single HeLa cell (the chromosome and nucleus having been labeled by the introduction of a GFP-histone fusion gene), and image classification according to the present embodiment was performed using the thus-obtained plurality of time-series images successively showing the phases of cell division. Specifically, the training image group included a plurality of time-series images (FIG. 20) that successively show the G2 phase (G2), prophase (pro), prometaphase (prometa), metaphase (meta), anaphase/telophase (ana/telo), and G1 phase (G1) of the HeLa cell, the classifier generation mode was executed using the training image group, and the classification mode was executed with use of the resulting classifier.

Figure 21A:
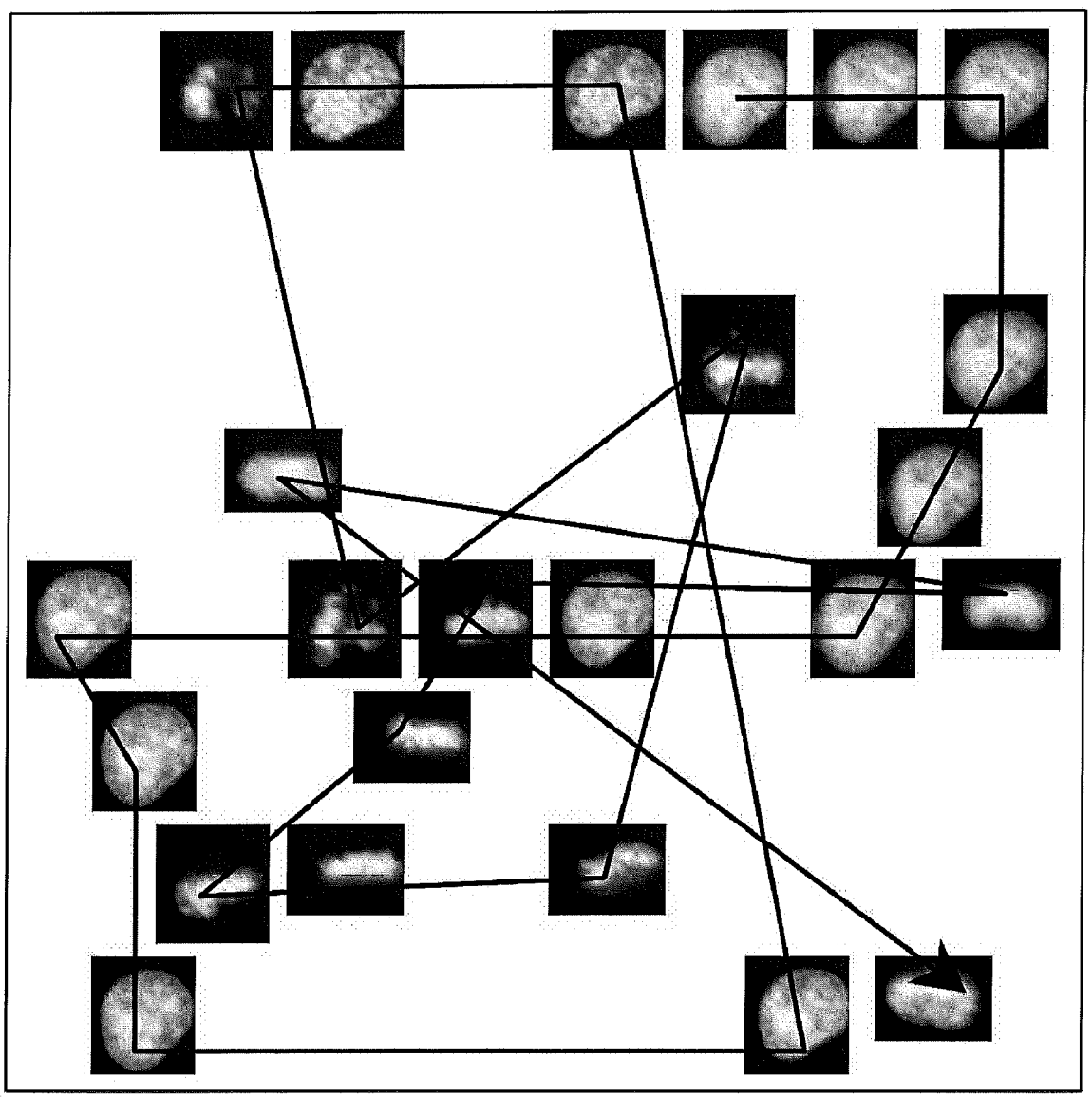
FIG. 21A is a diagram showing a feature map obtained by initial clustering executed in the classifier generation mode, in which the temporal before/after relationship between images is indicated by an arrow.

FIG. 21A is a diagram showing a feature map obtained by initial clustering executed in the classifier generation mode, in which the temporal before/after relationship between images (the transition in conditions of the cell that is the imaging target, that is to say, the transition from the G2 period before cell division, through the various phases of division, and then to the G1 phase after division) is indicated by an arrow. After the initial clustering, likewise to the above embodiment, the evaluation value of the feature map is calculated by performing normalization by dividing the "distance between trajectories indicating transitions in the conditions of the imaging targets" by the "sum of all of the inter-node degrees of similarity", and then subtracting the normalized value from 1.

Figure 21B:
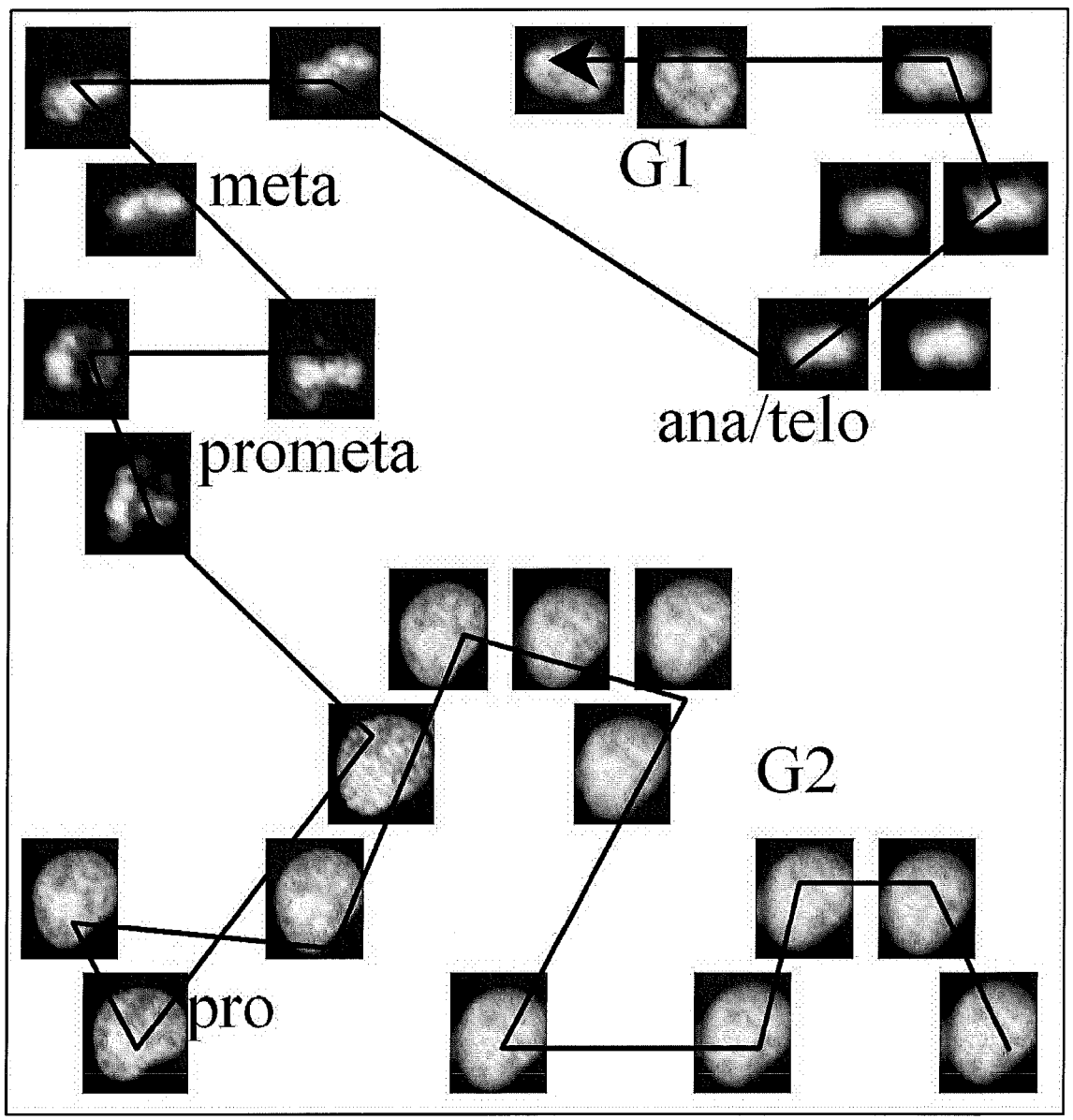
FIG. 21B is a diagram showing a feature map obtained as a result of applying a genetic algorithm, in which the temporal before/after relationship between images is indicated by an arrow.

FIG. 21B is a diagram showing a feature map obtained as a result of applying a genetic algorithm so as to obtain a high feature map evaluation value calculated as described above. In FIG. 21B as well, likewise to FIG. 21A, the temporal before/after relationship between images is shown by an arrow. By referencing FIG. 21B, it can be confirmed that the various cell cycle phases are grouped together in the feature map. This means that the feature quantity combination pattern that was selected is effective in the cell cycle phase evaluation.

Note that many improvements to and other embodiments of the present invention will be obvious to a person skilled in the art from the above description. Accordingly, the above description should be interpreted as merely exemplary, and has been provided with the object of teaching a person skilled in the art a preferred embodiment for implementing the present invention. Details of the structure and/or functions of the present invention can be substantially changed without departing from the spirit of the present invention.

INDUSTRIAL APPLICABILITY

A feature quantity selection method and image classification method of the present invention are useful to medical diagnosis, cytotoxicity determination, drug discovery screening, the detection of the effects of drugs such as endocrine disruptors, environment monitoring, and the analysis of unknown cell division specific substances.

The invention claimed is:

1. A feature quantity selection method comprising:
   a step (a) of clustering a plurality of training images for each of a plurality of combination patterns of a plurality of feature quantities that an image has; and
   a step (b) of selecting, from among the plurality of combination patterns, a classification-use combination pattern to be used in image classification, based on a result of the clustering,
   wherein the clustering is performed based on degrees of similarity between the training images that have been calculated with use of the feature quantities constituting the combination patterns.

2. The feature quantity selection method according to claim 1,
   wherein the step (a) and the step (b) are performed repeatedly, and the plurality of combination patterns in the second and onward performances of the step (a) are a classification-use combination pattern selected in the previous performance of the step (b).

3. The feature quantity selection method according to claim 1,
   wherein the step (a) includes a step (a1) of generating a map in which the plurality of training images are arranged at separation intervals in accordance with the degrees of similarity, and
   in the step (b), the classification-use combination pattern is selected based on the map generated in the step (a1).

4. The feature quantity selection method according to claim 3,
   wherein in the step (b), an evaluation value of the map generated in the step (a1) is calculated based on an annotation performed on the map, and the classification-use combination pattern is selected based on the calculated evaluation value of the map.

5. The feature quantity selection method according to claim 4,
   wherein in the step (b), the evaluation value of the map generated in the step (a1) is calculated based on an annotation performed on a portion of training images among the plurality of training images included in the map.

6. The feature quantity selection method according to claim 3,
   wherein in the step (b), the clustering is performed repeatedly with use of a combinatorial optimizing algorithm, based on the feature quantities that the image has, the combination patterns of feature quantities, and the calculated evaluation values of the maps.

7. The feature quantity selection method according to claim 3,
   wherein in the step (b), the clustering is performed repeatedly with use of a genetic algorithm, the feature quantities that the image has respectively being genetic loci, the combination patterns of feature quantities respectively being entities having genes whose elements are the genetic loci, and the calculated evaluation values of the maps respectively being fitnesses of the entities.

8. The feature quantity selection method according to claim 1,
   wherein the image is a captured image obtained by imaging a biological sample, and
   among the feature quantities are a shape feature quantity derived from a shape of the biological sample, and a texture feature quantity derived from a texture of the captured image.

9. An image classification method comprising:
   a step (a) of clustering a plurality of training images for each of a plurality of combination patterns of a plurality of feature quantities that an image has;
   a step (b) of selecting, from among the plurality of combination patterns, a classification-use combination pattern to be used in image classification, based on a result of the clustering; and
   a step (c) of classifying an input image with use of the classification-use combination pattern selected in the step (b),
   wherein the clustering is performed based on degrees of similarity between the training images that have been calculated with use of the feature quantities constituting the combination patterns.

10. A feature quantity selection apparatus comprising:
    a feature quantity selection unit that selects, from among a plurality of combination patterns of a plurality of feature quantities that an image has, a classification-use combination pattern to be used in image classification,
    the feature quantity selection unit performing
    a step (a) of clustering a plurality of training images for each of the plurality of combination patterns, and
    a step (b) of selecting the classification-use combination pattern based on a result of the clustering,
    wherein the clustering is performed based on degrees of similarity between the training images that have been calculated with use of the feature quantities constituting the combination patterns.

11. An image classification apparatus comprising:
    a feature quantity selection unit that selects, from among a plurality of combination patterns of a plurality of feature quantities that an image has, a classification-use combination pattern to be used in image classification; and
    an image classification unit that classifies an input image with use of the classification-use combination pattern selected by the feature quantity selection unit,
    the feature quantity selection unit performing
    a step (a) of clustering a plurality of training images for each of the plurality of combination patterns, and
    a step (b) of selecting the classification-use combination pattern based on a result of the clustering,
    wherein the clustering is performed based on degrees of similarity between the training images that have been calculated with use of the feature quantities constituting the combination patterns.

* * * * *